(12) United States Patent
Ebright et al.

(10) Patent No.: US 9,133,155 B2
(45) Date of Patent: Sep. 15, 2015

(54) ANTIBACTERIAL AGENTS: HIGH-POTENCY MYXOPYRONIN DERIVATIVES

(75) Inventors: Richard H. Ebright, New Brunswick, NJ (US); Yon W. Ebright, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/822,935

(22) PCT Filed: Sep. 16, 2011

(86) PCT No.: PCT/US2011/052015
§ 371 (c)(1),
(2), (4) Date: May 22, 2013

(87) PCT Pub. No.: WO2012/037508
PCT Pub. Date: Mar. 22, 2012

(65) Prior Publication Data
US 2013/0237595 A1  Sep. 12, 2013

Related U.S. Application Data

(60) Provisional application No. 61/384,162, filed on Sep. 17, 2010.

(51) Int. Cl.
| | |
|---|---|
| A61K 31/35 | (2006.01) |
| C07D 309/38 | (2006.01) |
| A61K 9/00 | (2006.01) |
| A61K 31/366 | (2006.01) |
| A61K 47/18 | (2006.01) |
| A61K 47/44 | (2006.01) |
| C07D 309/22 | (2006.01) |
| A01N 47/12 | (2006.01) |
| C12N 9/99 | (2006.01) |

(52) U.S. Cl.
CPC .............. *C07D 309/38* (2013.01); *A01N 47/12* (2013.01); *A61K 9/0019* (2013.01); *A61K 31/366* (2013.01); *A61K 47/18* (2013.01); *A61K 47/44* (2013.01); *C07D 309/22* (2013.01); *C12N 9/99* (2013.01)

(58) Field of Classification Search
USPC .......................................... 514/460; 549/291
See application file for complete search history.

(56) References Cited

U.S. PATENT DOCUMENTS

| 4,061,769 A | 12/1977 | Ohno et al. |
| 4,421,763 A | 12/1983 | Hamano et al. |
| 6,022,983 A * | 2/2000 | Wuonola et al. ............ 549/291 |
| 6,169,181 B1 | 1/2001 | Romines et al. |
| 6,191,288 B1 | 2/2001 | Ramamoorthy |
| 6,228,882 B1 | 5/2001 | Wuonola et al. |
| 8,772,332 B2 | 7/2014 | Ebright |
| 2003/0065039 A1 | 4/2003 | Kharazmi et al. |
| 2005/0187170 A1 | 8/2005 | Bantia et al. |
| 2006/0100291 A1 | 5/2006 | Perry et al. |
| 2007/0292355 A1 | 12/2007 | Tamarkin et al. |
| 2013/0289128 A1 | 10/2013 | Ebright et al. |

FOREIGN PATENT DOCUMENTS

| WO | WO 2007/094799 A1 | 8/2007 |
| WO | WO 2012/033846 A1 | 3/2012 |

OTHER PUBLICATIONS

Hu's CAS: 134: 100670, 2000.*
Mukhopadhyay et al. CAS: 150: 70642, 2008.*
Doundoulakis et al. CAS: 142: 56035, 2004.*
Andre et al. "Novel synthetic molecules targeting the bacterial RNA polymerase assembly", *Journal of Antimicrobial Chemotherapy*, 57, 245-251 (2006).
Chatterjee et al., "Isolation and structure of archangelenone. Flavonoid constituent of *Angelica archangelica*", XP002692911, Database Caplus [Online] Chemical Abstracts accession No. 1973:489536.
Doundoulakis et al., "Myxopyronin B analogs as inhibitors of RNA polymerase, synthesis and biological evaluation", *Bioorganic & Medicinal Chemistry Letters 14*, 5667-5672 (2004).
Lira et al., "Syntheses of novel myxopyronin B analogs as potential inhibitors of bacterial RNA polymerase", *Bioorganic & Medicinal Chemistry Letters 17*, 6797-6800 (2007).
Mukhopadhyay et al., "The RNA Polymerase "Switch Region" is a Target for Inhibitors", *Cell 135*, 295-307 (2008).
Patent Cooperation Treaty, International Searching Authority, Search Report and Written Opinion for PCT/US11/52015, 11 pages, Feb. 23, 2012.
Werner et al., "Synthesis of non-natural flavanones and dihydrochalcones in metabolically engineered yeast", *Journal of Molecular Catalysis B: Enzymatic 66*, 257-26 (2010).

* cited by examiner

*Primary Examiner* — Rei-Tsang Shiao
(74) *Attorney, Agent, or Firm* — Viksnins Harris & Padys PLLP

(57) ABSTRACT

The invention provides compounds of Formula (I) and pharmaceutically acceptable salts thereof, wherein Ya, Yb, R1, R2, and G are as described in the specification, as well as compositions comprising a compound of formula (I). The compounds are useful as inhibitors of bacterial RNA polymerase and as antibacterial agents.

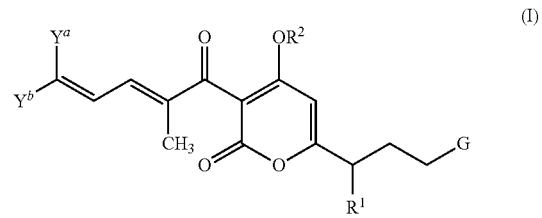

9 Claims, No Drawings

ANTIBACTERIAL AGENTS: HIGH-POTENCY MYXOPYRONIN DERIVATIVES

PRIORITY OF INVENTION

This application claims priority from U.S. Provisional Application No. 61/384,162, filed 17 Sep. 2010.

GOVERNMENT FUNDING

The invention described herein was made with United States Government support under Grant Numbers ROI-AI072766 and R01-AI90837 awarded by the National Institutes of Health. The United States Government has certain rights in the invention.

BACKGROUND OF THE INVENTION

Bacterial infectious diseases kill 100,000 persons each year in the US and 11 million persons each year worldwide, representing nearly a fifth of deaths each year worldwide (Heron et al., *Final Data for* 2006. *National Vital Statistics Reports, Vol.* 57 (Centers for Disease Control and Prevention, Atlanta Ga.) and World Health Organization (2008) *The Global Burden of Disease:* 2004 *Update* (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports,* 122, 160-166; Scott, R. (2009) *The direct medical costs of healthcare-associated infections in U.S. hospitals and benefits of prevention* (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a proven target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* in press, http:/dx.doi.org/doi:10.1016/j.mib.2011.07.030). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are highly conserved in human RNAP I, RNAP II, and RNAP III (permitting therapeutic selectivity).

The rifamycin antibacterial agents function by binding to and inhibiting bacterial RNAP (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). The rifamycins bind to a site on bacterial RNAP adjacent to the RNAP active center and prevent extension of RNA chains beyond a length of 2-3 nt. The rifamycins are in current clinical use in treatment of both Gram-positive and Gram-negative bacterial infections. The rifamycins are of particular importance in treatment of tuberculosis; the rifamycins are first-line anti-tuberculosis agents and are among the few antituberculosis agents able to kill non-replicating tuberculosis bacteria.

The clinical utility of the rifamycin antibacterial agents is threatened by the existence of bacterial strains resistant to rifamycins (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). Resistance to rifamycins typically involves substitution of residues in or immediately adjacent to the rifamycin binding site on bacterial RNAP—i.e., substitutions that directly decrease binding of rifamycins.

In view of the public-health threat posed by rifamycin-resistant and multidrug-resistant bacterial infections, there is an urgent need for new antibacterial agents that (i) inhibit bacterial RNAP (and thus have the same biochemical effects as rifamycins), but that (ii) inhibit bacterial RNAP through binding sites that do not overlap the rifamycin binding site (and thus do not share cross-resistance with rifamycins).

A new drug target—the "switch region"—within the structure of bacterial RNAP has been identified (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* in press, http:/dx.doi.org/doi:10.1016/j.mib.2011.07.030). The switch region is a structural element that mediates conformational changes required for RNAP to bind and retain the DNA template in transcription. The switch region is located at the base of the RNAP active-center cleft and serves as the hinge that mediates opening of the active-center cleft to permit DNA binding and that mediates closing of the active-center cleft to permit DNA retention. The switch region can serve as a binding site for compounds that inhibit bacterial gene expression and kill bacteria. Since the switch region is highly conserved in bacterial species, compounds that bind to the switch region are active against a broad spectrum of bacterial species. Since the switch region does not overlap the rifamycin binding site, compounds that bind to the switch region are not cross-resistant with rifamycins.

It has been shown that the α-pyrone antibiotic myxopyronin (Myx) functions through interactions with the bacterial RNAP switch region (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* in press, http:/dx.doi.org/doi:10.1016/j.mib.2011.07.030). Myx binds to the RNAP switch region, traps the RNAP switch region in a single conformational state, and interferes with formation of a catalytically competent transcription initiation complex. Amino acid substitutions within RNAP that confer resistance to Myx occur only within the RNAP switch region. There is no overlap between amino acid substitutions that confer resistance to Myx and amino acid substitutions that confer resistance to rifamycins and, accordingly, there is no cross-resistance between Myx and rifamycins.

A crystal structure of a non-pathogenic bacterial RNAP, *Thermus thermophilus* RNAP, in complex with Myx has been determined, and homology models of pathogenic bacterial RNAP, including *Mycobacterium tuberculosis* RNAP and *Staphylococcus aureus* RNAP, in complex with Myx have been constructed (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin.*

Struct. Biol. 19, 715-723; Srivastava et al. (2011) Curr. Opin. Microbiol. in press, http:/dx.doi.org/doi:10.1016/j.mib.2011.07.030). The crystal structure and homology models define interactions between RNAP and Myx and can be used to understand the roles of the "west" and "east" Myx sidechains as well as the Myx α-pyrone core.

An object of this invention is to provide compounds that have utility as inhibitors of bacterial RNAP.

An object of this invention is to provide compounds that have utility as inhibitors of bacterial growth.

A particular object of this invention is to provide compounds and pharmaceutical compositions that have utility in the treatment of bacterial infection in a mammal.

DETAILED DESCRIPTION OF THE INVENTION

Definitions

The following definitions are used, unless otherwise indicated.

The term "halo" means fluoro, chloro, bromo, or iodo.

The term "alkyl" used alone or as part of a larger moiety, includes both straight and branched chains containing one to twelve carbon atoms.

The term "alkenyl" used alone or as part of a larger moiety, includes both straight and branched chains containing two to twelve carbon atoms and one or more (e.g. 1 or 2) double bonds. The term also includes "$C_2$-$C_{12}$ straight or branched monoalkene" which is a $C_2$-$C_{12}$ straight or branched chain containing one double bond. The term also includes "$C_5$-$C_{12}$ straight or branched alkadienyl" which is a $C_5$-$C_{12}$ straight or branched chain containing two double bonds.

The term "alkynyl", used alone or as part of a larger moiety, includes both straight and branched chains containing two to twelve carbon atoms and one or more (e.g. 1 or 2) triple bonds.

The term "cycloalkyl, used alone or as part of a larger moiety, includes cyclic $C_3$-$C_{12}$ hydrocarbons which are completely saturated or which contain one or more units of unsaturation, but which are not aromatic.

The term alkoxy refers to a group of formula alkyl-O—.

The terms "haloalkyl", "haloalkenyl" and "haloalkoxy", mean alkyl, alkenyl or alkoxy, as the case may be, substituted with one or more (e.g. 1, 2, 3, or 4) halogen atoms. The term haloalkoxy also includes "$C_1$-$C_4$ trifluoroalkoxy" which is a $C_1$-$C_4$ alkoxy group that is substituted with three fluoro groups.

The term "hydroxyalkyl" includes alkyl substituted with one, two, or three hydroxy groups. The term also includes "$C_2$-$C_{12}$ straight or branched hydroxyalkyl" which is a $C_2$-$C_{12}$ alkyl group substituted with one, two, or three hydroxy groups.

The term "hydroxyalkenyl" includes a $C_2$-$C_{12}$ alkenyl substituted with one, two, or three hydroxy groups. The term also includes "$C_2$-$C_{12}$ straight or branched (hydroxy)monoalkenyl" which is a $C_2$-$C_{12}$ straight or branched chain containing one double bond and one, two, or three hydroxy groups. The term also includes "$C_5$-$C_{12}$ straight or branched hydroxyalkadienyl" which is a $C_5$-$C_{12}$ straight or branched chain containing two double bonds and one, two, or three hydroxy groups.

The term $C_7$-$C_{12}$ aralkyl includes an (aryl)alkyl-group having 7-12 carbon atoms, for example a benzyl or phenethyl group.

The term $C_7$-$C_{12}$ (aryl)hydroxyalkyl includes a (aryl)alkyl-group having 7-12 carbon atoms that is substituted on the alkyl portion with one or more (e.g. 1, 2, 3, or 4) hydroxy groups.

The term "$C_6$-$C_{12}$ heteroaralkyl" includes a group (heteroaryl)alkyl- having 6-12 carbon atoms, for example, 2-pyridylmethyl or 2-pyrid-2-ylethyl.

The term "$C_6$-$C_{12}$ (heteroaryl)hydroxyalkyl" includes a group (heteroaryl)alkyl-having 6-12 carbon atoms that is substituted on the alkyl portion with one or more (e.g. 1, 2, 3, or 4) hydroxy groups.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2-pyrrolyl), NH (as in pyrrolidinyl) or NR$^+$ (as in N-substituted pyrrolidinyl).

The term "aryl" used alone or as part of a larger moiety as in "aralkyl", "aralkoxy", or "aryloxyalkyl", refers to aromatic ring groups having five to fourteen members, such as phenyl, 1-naphthyl, 2-naphthyl, 1-anthracyl and 2-anthracyl. "Aryl" also includes fused polycyclic aromatic ring systems in which an aromatic ring is fused to one or more non-aromatic rings, such as in an indanyl, phenanthridinyl, or tetrahydronaphthyl, where the radical or point of attachment is on the aromatic ring. The term "aryl" also refers to aromatic rings and fused polycyclic aromatic ring systems that are optionally substituted, for example, with one or more groups independently selected from halogen, alkyl, alkenyl, alkynyl, cycloalkyl, hydroxy, cyano, alkoxy, haloalkyl, haloalkoxy, alkylcarbonyl, alkoxycarbonyl, alkyl-C(=O)—O—, and —NR$_a$R$_b$; wherein each R$_a$ and R$_b$ is independently selected from H, alkyl, and alkylcarbonyl. The term "aryl" may be used interchangeably with the term "aryl ring".

The term "heterocycle", "heterocyclyl", or "heterocyclic" as used herein includes non-aromatic ring systems having three to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. Bridged ring systems are also included within the scope of the term "heterocyclyl" or "heterocyclic". The term "heterocycle", "heterocyclyl", or "heterocyclic" whether saturated or partially unsaturated, also refers to heterocyclic rings that are optionally substituted, for example, with one or more groups independently selected from oxo (=O), halogen, alkyl, alkenyl, alkynyl, cycloalkyl, hydroxy, cyano, alkoxy, haloalkyl, haloalkoxy, alkylcarbonyl, alkoxycarbonyl, alkyl-C(=O)—O—, and —NR$_a$R$_b$; wherein each R$_a$ and R$_b$ is independently selected from H, alkyl, and alkylcarbonyl.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to heteroaromatic rings that are optionally substituted, for example, with one or more groups independently selected from halogen, alkyl, alkenyl, alkynyl, cycloalkyl, hydroxy, cyano, alkoxy, haloalkyl, haloalkoxy, alkylcarbonyl, alkoxycarbonyl, alkyl-C(=O)—O—, and —NR$_a$R$_b$; wherein each R$_a$ and R$_b$ is independently selected from H, alkyl, and alkylcarbonyl. The term "heteroaryl" may be used interchangeably with the term "heteroaryl ring" or the term "heteroaromatic."

A combination of substituents or variables is permissible only if such a combination results in a stable or chemically feasible compound. The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Antibacterial Agents

This invention provides novel compounds that contain alterations of the Myx "west" sidechain that, it is believed, may have one or more of the following advantages relative to the Myx native "west" side chain: (1) improvement of interactions with the bacterial-RNAP Myx binding site and an adjacent hydrophobic pocket, (2) increased potency of antibacterial activity, (3) broadened spectrum of antibacterial activity, (4) reduction of losses of interactions with the bacterial-RNAP Myx binding site and an adjacent hydrophobic pocket that occur upon E-to-Z isomerization of the "west"-most double bond of the Myx "west" sidechain, and (5) reduction of binding to serum proteins.

Said compounds contain an "east" sidechain that, it is believed, may form most or all of the same hydrogen-bonded interactions with the bacterial-RNAP Myx binding site that are formed by the Myx native "east" sidechain.

The compounds of this invention have utility as RNAP inhibitors.

The compounds of this invention have utility as antibacterial agents.

In one aspect, the invention provides a compound of Formula I:

or a pharmaceutically acceptable salt thereof, wherein:

$R^1$ is hydrogen or —$CH_3$;

$R^2$ is hydrogen or —$C_1$-$C_6$ straight or branched alkyl;

one of $Y^a$ and $Y^b$ is hydrogen or $C_1$-$C_4$ straight alkyl, and the other of $Y^a$ and $Y^b$ is $C_1$-$C_{10}$ straight or branched alkyl, $C_2$-$C_{12}$ straight or branched hydroxyalkyl, $C_2$-$C_{12}$ straight or branched alkenyl, $C_2$-$C_{12}$ straight or branched hydroxyalkenyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $Y^a$ and $Y^b$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl or hydroxyalkyl groups, wherein an alkyl, aryl or heteroaryl moiety of $Y^a$ and $Y^b$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —$SO_2$($C_1$-$C_4$ alkyl);

G is —CH═CH—NHC(O)—$R^3$, —CH═CH—NHC(S)—$R^3$, —$CH_2CH_2$NHC(O)—$R^3$, —$CH_2CH_2$NHC(S)—$R^3$, —$CH_2$NHNHC(O)—$R^3$, or —$CH_2$NHNHC(S)—$R^3$;

$R^3$ is $C_1$-$C_6$ alkyl, —O($C_1$-$C_6$ alkyl), —S($C_1$-$C_6$ alkyl), or —N($R^4$)$_2$; and each $R^4$ is independently hydrogen or —$C_1$-$C_6$ alkyl;

provided that, when $Y^a$ is hydrogen and $Y^b$ is —$CH_2CH_2CH_2CH_3$, or when $Y^a$ is —$CH_3$ and $Y^b$ is —$CH_2CH_2CH$═C($CH_3$)$_2$, —$CH_2CH_2$CH(OH)C($CH_3$)═$CHCH_2$CH═$CHCH_3$, or —$CH_2CH_2$CH(OH)C($CH_3$)═$CHCH_2$CH═$CHCH_2$CH$_3$, then G is other than —CH═CH—NHC(O)—$OCH_3$; and provided that, when $Y^a$ is —$CH_3$ and $Y^b$ is —$CH_2CH_2CH_3$ or —$CH_2CH_2CH_2CH_3$, then G is other than —CH═CH—NHC(O)—($C_1$-$C_6$ alkyl), —CH═CH—NHC(O)—O($C_1$-$C_6$ alkyl), —CH═CH—NHC(O)—N($R^4$)$_2$, and —$CH_2CH_2$—NHC(O)—O($C_1$-$C_6$ alkyl).

$R^1$ may be hydrogen or methyl. When le is —$CH_3$, it will be attached to chiral carbon. With respect to this chiral center, compounds of Formula I may exist in either the R or S configuration or as mixture of stereoisomers. One embodiment relates to compounds of Formula I where $R^1$ is —$CH_3$ and the carbon to which it is attached is predominantly the R isomer, preferably at least 90% of the R isomer shown below:

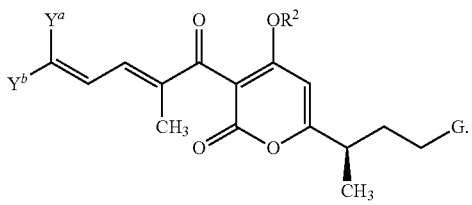

$R^2$ is preferably hydrogen.

Together, $Y^a$ and $Y^b$ provide a hydrophobic moiety that can extend the length of about a 10 carbon chain extending from the diene portion of the molecule. With respect to the double bond directly attached to $Y^a$ and $Y^b$, the double bond stereochemistry may be either E (trans) or Z (cis). The other double bond of the diene (the one closer to the pyrone ring) is preferably the E isomer.

In one embodiment, $Y^a$ and $Y^b$ are unsubstituted. When $Y^a$ or $Y^b$ are substituted, examples of suitable substituents include halo, such as chloro and fluoro; alkoxy, such as methoxy and ethoxy; hydroxyalkyl, such as hydroxymethyl, hydroxyethyl or 1- or 2-hydroxypropyl; cyano; and methylsulfonyl.

In one embodiment, one of $Y^a$ and $Y^b$ is hydrogen, —$CH_3$, —$CH_2CH_3$, —$CH_2CH_2CH_3$, or —$CH_2CH_2CH_2CH_3$, and the other of $Y^a$ and $Y^b$ is $C_1$-$C_{10}$ straight or branched alkyl, $C_2$-$C_{12}$ straight or branched alkenyl, $C_7$-$C_{10}$ aralkyl, or $C_6$-$C_{10}$ heteroaralkyl.

In another embodiment, one of $Y^a$ and $Y^b$ is hydrogen, —$CH_3$, —$CH_2CH_3$, —$CH_2CH_2CH_3$, or —$CH_2CH_2CH_2CH_3$, and the other of $Y^a$ and $Y^b$ is $C_1$-$C_{10}$ straight or branched alkyl, or $C_2$-$C_{12}$ straight or branched alkenyl.

In another embodiment, one of $Y^a$ and $Y^b$ is hydrogen or —$CH_3$, and the other of $Y^a$ and $Y^b$ is $C_1$-$C_{10}$ straight or branched alkyl, or $C_2$-$C_{12}$ straight or branched alkenyl.

In another embodiment, one of $Y^a$ and $Y^b$ is hydrogen or —$CH_3$, and the other of $Y^a$ and $Y^b$ is $C_1$-$C_{10}$ straight or branched alkyl, $C_2$-$C_{12}$ straight or branched alkenyl, or $C_2$-$C_{12}$ straight or branched hydroxyalkenyl.

In another embodiment, one of $Y^a$ and $Y^b$ is hydrogen or —$CH_3$, and the other of $Y^a$ and $Y^b$ is $C_1$-$C_{10}$ straight or branched alkyl, $C_5$-$C_{12}$ straight or branched alkadienyl, or $C_5$-$C_{12}$ straight or branched hydroxyalkadienyl.

In another embodiment, one of $Y^a$ and $Y^b$ is —$CH_3$, and the other of $Y^a$ and $Y^b$ is $C_1$-$C_{10}$ straight or branched alkyl, or $C_2$-$C_{12}$ straight or branched alkenyl.

In another embodiment, one of $Y^a$ and $Y^b$ is —$CH_3$, and the other of $Y^a$ and $Y^b$ is $C_1$-$C_{10}$ straight or branched alkyl, $C_2$-$C_{12}$ straight or branched alkenyl, or $C_2$-$C_{12}$ straight or branched hydroxyalkenyl.

In another embodiment, one of $Y^a$ and $Y^b$ is —$CH_3$, and the other of $Y^a$ and $Y^b$ is $C_1$-$C_{10}$ straight or branched alkyl, $C_5$-$C_{12}$ straight or branched alkadienyl, or $C_5$-$C_{12}$ straight or branched hydroxyalkadienyl.

In another embodiment one of $Y^a$ and $Y^b$ is hydrogen or $C_1$-$C_4$ straight alkyl, and the other of $Y^a$ and $Y^b$ is $C_1$-$C_{10}$ straight or branched alkyl, $C_2$-$C_{12}$ straight or branched hydroxyalkyl, $C_5$-$C_{12}$ straight or branched alkadienyl, $C_2$-$C_{12}$ straight or branched (hydroxy)monoalkenyl, $C_5$-$C_{12}$ straight or branched hydroxyalkadienyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $Y^a$ and $Y^b$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl, or hydroxyalkyl groups, wherein an alkyl, aryl or heteroaryl moiety of $Y^a$ and $Y^b$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —$SO_2$($C_1$-$C_4$ alkyl).

Examples of $Y^a$ and $Y^b$ straight or branched alkyl groups include the following: $CH_3$—($CH_2$)$_p$—$CH_2$—, where p is 1-8, ($CH_3$)$_2$CH($CH_2$)$_q$—$CH_2$—, where q is 1-7, $CH_3$($CH_2$)$_n$CH($CH_3$)$CH_2CH_2$—, where r is 1-3 and ($CH_3$)$_2$CH(CH)$_n$CH($CH_3$)$CH_2CH_2$—, where s is 1 or 2.

Examples of $Y^a$ and $Y^b$ $C_2$-$C_{12}$ straight or branched alkenyl groups or $C_5$-$C_{12}$ straight or branched alkadienyl groups include ($CH_3$)$_2$C═CH($CH_2$)$_t$—$CH_2$—, $CH_2$═C($CH_3$)$CH_2$($CH_2$)$_t$—$CH_2$—, $CH_3$CH═$CHCH_2$CH═C($CH_3$)$CH_2CH_2CH_2$—, ($CH_3$)$_2$C═$CHCH_2$CH═C($CH_3$)$CH_2CH_2CH_2$—, where t is 1-5. In one embodiment, $Y^a$ or $Y^b$ is ($CH_3$)$_2$C═$CHCH_2CH_2$— or $CH_2$═C($CH_3$)$CH_2CH_2CH_2$—.

Examples of $Y^a$ or $Y^b$ $C_2$-$C_{10}$ straight or branched hydroxyalkyl, or $C_2$-$C_{12}$ straight or branched hydroxyalkenyl groups include the specific groups disclosed above except having an —OH substituent on the third carbon extending from the diene portion of the molecule.

More specific examples of $Y^a$ and $Y^b$ include hydrogen, methyl, ethyl, propyl, butyl, ($CH_3$)$_2$C═$CHCH_2CH_2$—, ($CH_3$)$_2$C═CH($CH_2$)$_t$—$CH_2$—, $CH_2$═C($CH_3$)$CH_2$($CH_2$)$_t$—$CH_2$—, $CH_2$═C($CH_3$)CH(OH)($CH_2$)$_t$—$CH_2$—, $CH_3$CH═$CHCH_2$CH═C($CH_3$)$CH_2CH_2CH_2$—, ($CH_3$)$_2$C═$CHCH_2$CH═C($CH_3$)$CH_2CH_2CH_2$—, $CH_3$CH═$CHCH_2$CH═C($CH_3$)CH(OH)$CH_2CH_2$—, or ($CH_3$)$_2$C═$CHCH_2$CH═C($CH_3$)CH(OH)$CH_2CH_2$—, where t is 1 to 5. In one aspect, t is 2 or 3.

One embodiment provides a compound of Formula I where $R^2$ is hydrogen; one of $Y^a$ and $Y^b$ is hydrogen or $C_1$-$C_4$ straight alkyl, and the other of $Y^a$ and $Y^b$ is $C_1$-$C_{10}$ straight or branched alkyl, $C_2$-$C_{12}$ straight or branched hydroxyalkyl, $C_2$-$C_{12}$ straight or branched alkenyl or $C_2$-$C_{12}$ straight or branched hydroxyalkenyl, or $Y^a$ and $Y^b$ are taken together with their intervening atom to form a 4-6 membered ring having 0-1 ring heteroatoms selected from nitrogen, oxygen or sulfur; G is —CH=CH—NHC(O)—$R^3$, —CH=CH—NHC(S)—$R^3$, —CH$_2$CH$_2$NHC(O)—$R^3$, —CH$_2$CH$_2$NHC(S)—$R^3$, —CH$_2$NHNHC(O)—$R^3$, or —CH$_2$NHNHC(S)—$R^3$; $R^3$ is $C_1$-$C_6$ alkyl, —O($C_1$-$C_6$ alkyl), —S($C_1$-$C_6$ alkyl), or —N($R^4$)$_2$; and one $R^4$ is hydrogen and the other $R^4$ is hydrogen or —$C_1$-$C_6$ alkyl.

Another embodiment provides a compound of Formula I where one of $Y^a$ and $Y^b$ is hydrogen or —CH$_3$, and the other of $Y^a$ and $Y^b$ is $C_1$-$C_{10}$ straight or branched alkyl, $C_2$-$C_{12}$ straight or branched hydroxyalkyl, $C_2$-$C_{12}$ straight or branched alkenyl, or $C_2$-$C_{12}$ straight or branched hydroxyalkenyl; G is —CH=CH—NHC(O)—$R^3$, —CH$_2$CH$_2$NHC(O)—$R^3$, or —CH$_2$NHNHC(O)—$R^3$; $R^3$ is $C_1$-$C_6$ alkyl, —O($C_1$-$C_6$ alkyl), or —N($R^4$)$_2$; and one $R^4$ is hydrogen and the other $R^4$ is hydrogen or —$C_1$-$C_4$ alkyl.

Another embodiment provides a compound of Formula I where one of $Y^a$ and $Y^b$ is hydrogen or —CH$_3$, and the other of $Y^a$ and $Y^b$ is $C_1$-$C_{10}$ alkyl, (CH$_3$)$_2$C=CH(CH$_2$)$_t$—CH$_2$—, CH$_2$=C(CH$_3$)CH$_2$(CH$_2$)$_t$—CH$_2$—, CH$_2$=C(CH$_3$)CH(OH)(CH$_2$)$_t$—CH$_2$—, CH$_3$CH=CHCH$_2$CH=C(CH$_3$)CH$_2$CH$_2$CH$_2$—, (CH$_3$)$_2$C=CHCH$_2$CH=C(CH$_3$)CH$_2$CH$_2$CH$_2$—, CH$_3$CH=CHCH$_2$CH=C(CH$_3$)CH(OH)CH$_2$CH$_2$—, or (CH$_3$)$_2$C=CHCH$_2$CH=C(CH$_3$)CH(OH)CH$_2$CH$_2$—, where t is one to five; G is —CH=CH—NHC(O)—$R^3$, —CH$_2$CH$_2$NHC(O)—$R^3$, or —CH$_2$NHNHC(O)—$R^3$; $R^3$ is —CH$_3$, —OCH$_3$, —NH$_2$, or —NHCH$_3$; and one $R^4$ is hydrogen and the other $R^4$ is hydrogen or methyl.

In another set of embodiments, one of $Y^a$ and $Y^b$ is hydrogen or —CH$_3$, and the other of $Y^a$ and $Y^b$ is butyl, pentyl, hexyl, heptyl, octyl, nonyl, decyl, (CH$_3$)$_2$C=CHCH$_2$CH$_2$—, CH$_2$=C(CH$_3$)CH$_2$(CH$_2$)$_t$—CH$_2$—, or CH$_2$=C(CH$_3$)CH(OH)(CH$_2$)$_t$—CH$_2$—, where t is 1 to 3, and G is as described in a preceding embodiment.

In another set of embodiments, one of $Y^a$ and $Y^b$ is —CH$_3$, and the other of $Y^a$ and $Y^b$ is butyl, (CH$_3$)$_2$C=CHCH$_2$CH$_2$—, CH$_2$=C(CH$_3$)CH$_2$(CH$_2$)$_t$—CH$_2$—, or CH$_2$=C(CH$_3$)CH(OH)(CH$_2$)$_t$—CH$_2$—, where t is 1 to 3, and G is as described in a preceding embodiment.

In one embodiment, G is —CH=CH—NHC(O)—$R^3$. In another embodiment, —CH$_2$CH$_2$NHC(O)—$R^3$. In another embodiment, G is —CH$_2$NHNHC(O)—$R^3$.

In another set of embodiments, G is —CH=CHNHCO$_2$CH$_3$, —CH=CHNHC(O)CH$_3$, —CH$_2$CH$_2$NHCO$_2$CH$_3$, —CH$_2$CH$_2$NHC(O)CH$_3$, —CH$_2$NH—NHCO$_2$CH$_3$, or —CH$_2$NH—NHC(O)CH$_3$; and $Y^a$, $Y^b$, $R^1$, and $R^2$ are as described in a preceding embodiment.

In another set of embodiments, G is —CH=CHNH—C(O)NH$_2$, —CH=CHNH—C(O)NHCH$_3$, —CH$_2$CH$_2$NHC(O)NH$_2$, —CH$_2$CH$_2$NHC(O)NHCH$_3$, —CH$_2$NH—NHC(O)NH$_2$, or —CH$_2$NH—NHC(O)NHCH$_3$; and $Y^a$, $Y^b$, $R^1$, and $R^2$ are as described in a preceding embodiment.

In another set of embodiments, $R^3$ is —CH$_3$, —CH$_2$CH$_3$, —OCH$_3$, —OCH$_2$CH$_3$, —NH$_2$, —NHCH$_3$, or —NHCH$_2$CH$_3$, and $Y^a$, $Y^b$, $R^1$, and $R^2$ are as described in a preceding embodiment.

One embodiment provides a compound of Formula I wherein $Y^a$ and $Y^b$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl or hydroxyalkyl groups, wherein an alkyl, aryl or heteroaryl moiety of $Y^a$ and $Y^b$ optionally is substituted with 1-3 groups independently selected from halo, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —SO$_2$($C_1$-$C_4$ alkyl). In one aspect of this embodiment, $Y^a$ and $Y^b$ are taken together with their intervening atom to form a cyclopentyl or cyclohexyl ring.

In one embodiment the invention provides a compound of formula I:

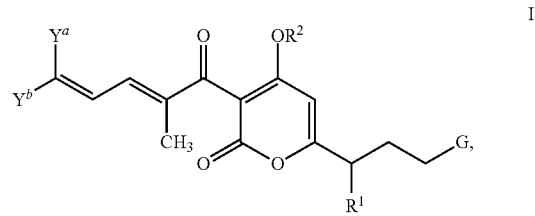

or a pharmaceutically acceptable salt thereof, wherein:

$R^1$ is hydrogen or —CH$_3$;

$R^2$ is hydrogen or —$C_1$-$C_6$ straight or branched alkyl;

one of $Y^a$ and $Y^b$ is hydrogen or $C_1$-$C_4$ straight alkyl, and the other of $Y^a$ and $Y^b$ is $C_1$-$C_{10}$ straight or branched alkyl, $C_2$-$C_{12}$ straight or branched hydroxyalkyl, $C_2$-$C_{12}$ straight or branched alkenyl, $C_2$-$C_{12}$ straight or branched hydroxyalkenyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $Y^a$ and $Y^b$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl, or hydroxyalkyl groups, wherein an alkyl, aryl or heteroaryl moiety of $Y^a$ and $Y^b$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —SO$_2$($C_1$-$C_4$ alkyl);

G is —CH=CH—NHC(O)—$R^3$, —CH=CH—NHC(S)—$R^3$, —CH$_2$CH$_2$NHC(O)—$R^3$, —CH$_2$CH$_2$NHC(S)—$R^3$, —CH$_2$NHNHC(O)—$R^3$, or —CH$_2$NHNHC(S)—$R^3$;

$R^3$ is $C_1$-$C_6$ alkyl, —O($C_1$-$C_6$ alkyl), —S($C_1$-$C_6$ alkyl), or —N($R^4$)$_2$; and each $R^4$ is independently hydrogen or —$C_1$-$C_6$ alkyl;

provided that, when $Y^a$ is hydrogen and $Y^b$ is —CH$_2$CH$_2$CH$_2$CH$_3$, or when $Y^a$ is —CH$_3$ and $Y^b$ is —CH$_2$CH$_2$CH=C(CH$_3$)$_2$, —CH$_2$CH$_2$CH$_2$OH, —CH$_2$CH$_2$CH$_2$OCH$_2$OCH$_3$, —CH$_2$CH$_2$CH(OH)C(CH$_3$)=CHCH$_2$CH=CHCH$_3$, or —CH$_2$CH$_2$CH(OH)C(CH$_3$)=CHCH$_2$CH=CHCH$_2$CH$_3$, then G is other than —CH=CH—NHC(O)—OCH$_3$;

and provided that, when $Y^a$ is —CH$_3$ and $Y^b$ is —$C_1$-$C_9$ alkyl, then G is other than —CH=CH—NHC(O)—($C_1$-$C_6$ alkyl), —CH=CH—NHC(O)—O($C_1$-$C_6$ alkyl), and —CH=CH—NHC(O)—N($R^4$)$_2$.

In one embodiment of the invention, the compound of formula I is a compound of formula Ia:

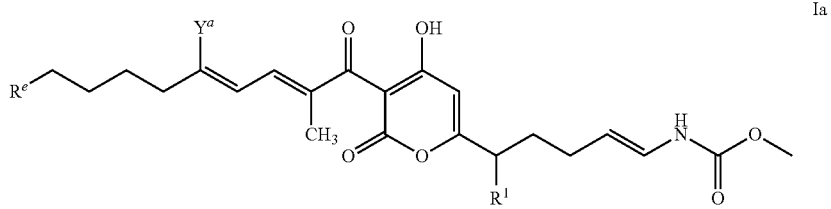

Ia wherein: $R^e$ is H, methyl, or ethyl, which methyl or ethyl optionally is substituted with hydroxy, —$C_1$-$C_4$ alkoxy, or halogen; $Y^a$ is H or methyl; and $R^1$ is H or methyl.

In one embodiment of the invention, when $Y^a$ is hydrogen and $Y^b$ is —$CH_2CH_2CH_2CH_3$, or when $Y^a$ is —$CH_3$ and $Y^b$ is —$CH_2CH_2CH_3$, —$CH_2CH_2CH_2CH_3$, —$CH_2CH_2CH$═C($CH_3$)$_2$, —$CH_2CH_2CH_2OH$, —$CH_2CH_2CH_2OCH_2OCH_3$, —$CH_2CH_2CH(OH)C(CH_3)$═$CHCH_2CH$═$CHCH_3$, or —$CH_2CH_2CH(OH)C(CH_3)$═$CHCH_2CH$═$CHCH_2CH_3$, then G is other than —CH═CH—NHC(O)—$OCH_3$; and when $Y^a$ is —$CH_3$ and $Y^b$ is unsubstituted —$C_1$-$C_{10}$ alkyl and le is methyl, then G is other than —CH═CH—NHC(O)—($C_1$-$C_6$ alkyl), —CH═CH—NHC(O)—O($C_1$-$C_6$ alkyl), —$CH_2CH_2NHC(O)$—O($C_1$-$C_6$ alkyl), and —CH═CH—NHC(O)—N($R^4$)$_2$.

In one embodiment of the invention, when $Y^a$ is hydrogen and $Y^b$ is —$CH_2CH_2CH_2CH_3$, or when $Y^a$ is —$CH_3$ and $Y^b$ is —$CH_2CH_2CH$═C($CH_3$)$_2$, —$CH_2CH_2CH_2OH$, —$CH_2CH_2CH_2OCH_2OCH_3$, —$CH_2CH_2CH(OH)C(CH_3)$═$CHCH_2CH$═$CHCH_3$, or —$CH_2CH_2CH(OH)C(CH_3)$═$CHCH_2CH$═$CHCH_2CH_3$, then G is other than —CH═CH—NHC(O)—$OCH_3$; and when $Y^a$ is —$CH_3$ and $Y^b$ is —$C_1$-$C_9$ alkyl, then G is other than —CH═CH—NHC(O)—($C_1$-$C_6$ alkyl), —CH═CH—NHC(O)—O($C_1$-$C_6$ alkyl), and —CH═CH—NHC(O)—N($R^4$)$_2$.

Examples of specific compounds of Formula I are shown in Tables 1 and 2 below.

TABLE 1

Examples of Specific Compounds of Formula I

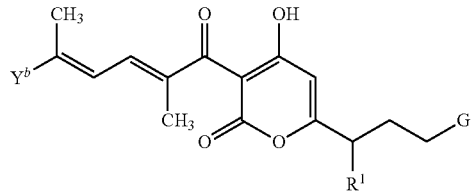

Examples of Specific Compounds of Formula I ($Y^a$ = $CH_3$ and $R^2$ = H)

| No. | $Y^b$ | $R^1$ | G |
|-----|-------|-------|---|
| 101 | $CH_3CH_2CH_2CH_2CH_2$— | H | —CH═CHNH—$CO_2CH_2CH_3$ |
| 102 | $CH_3CH_2CH_2CH_2CH_2$ | H | —CH═CHNH—C(O)$CH_3$ |
| 103 | $CH_3CH_2CH_2CH_2CH_2$— | H | —CH═CHNH—C(O)$CH_2CH_3$ |
| 104 | $CH_3CH_2CH_2CH_2CH_2$— | H | —CH═CHNH—C(O)$NHCH_3$ |
| 105 | $CH_3CH_2CH_2CH_2CH_2$— | H | —CH═CHNH—C(S)$OCH_3$ |
| 106 | $CH_3CH_2CH_2CH_2CH_2$— | H | —$CH_2CH_2NHCO_2CH_3$ |
| 107 | $CH_3CH_2CH_2CH_2CH_2$— | H | —$CH_2CH_2NHC(O)CH_3$ |
| 108 | $CH_3CH_2CH_2CH_2CH_2$— | H | —$CH_2CH_2NHC(O)NHCH_3$ |
| 109 | $CH_3CH_2CH_2CH_2CH_2$— | H | —$CH_2NH$—$NHCO_2CH_3$ |
| 110 | $CH_3CH_2CH_2CH_2CH_2$— | H | —$CH_2NH$—$NHC(O)CH_3$ |
| 112 | $CH_3CH_2CH_2CH_2CH_2$— | $CH_3$ | —CH═CHNH—$CO_2CH_2CH_3$ |
| 113 | $CH_3CH_2CH_2CH_2CH_2$ | $CH_3$ | —CH═CHNH—C(O)$CH_3$ |
| 114 | $CH_3CH_2CH_2CH_2CH_2$— | $CH_3$ | —CH═CHNH—C(O)$CH_2CH_3$ |
| 115 | $CH_3CH_2CH_2CH_2CH_2$— | $CH_3$ | —CH═CHNH—C(O)$NHCH_3$ |
| 116 | $CH_3CH_2CH_2CH_2CH_2$— | $CH_3$ | —CH═CHNH—C(S)$OCH_3$ |
| 117 | $CH_3CH_2CH_2CH_2CH_2$— | $CH_3$ | —$CH_2CH_2NHCO_2CH_3$ |
| 118 | $CH_3CH_2CH_2CH_2CH_2$— | $CH_3$ | —$CH_2CH_2NHC(O)CH_3$ |
| 119 | $CH_3CH_2CH_2CH_2CH_2$— | $CH_3$ | —$CH_2CH_2NHC(O)NHCH_3$ |
| 120 | $CH_3CH_2CH_2CH_2CH_2$— | $CH_3$ | —$CH_2NH$—$NHCO_2CH_3$ |
| 121 | $CH_3CH_2CH_2CH_2CH_2$— | $CH_3$ | —$CH_2NH$—$NHC(O)CH_3$ |
| 123 | $CH_3CH_2CH_2CH_2CH_2CH_2$— | H | —CH═CHNH—$CO_2CH_2CH_3$ |
| 124 | $CH_3CH_2CH_2CH_2CH_2CH_2$ | H | —CH═CHNH—C(O)$CH_3$ |
| 125 | $CH_3CH_2CH_2CH_2CH_2CH_2$— | H | —CH═CHNH—C(O)$CH_2CH_3$ |
| 126 | $CH_3CH_2CH_2CH_2CH_2CH_2$— | H | —CH═CHNH—C(O)$NHCH_3$ |
| 127 | $CH_3CH_2CH_2CH_2CH_2CH_2$— | H | —CH═CHNH—C(S)$OCH_3$ |
| 128 | $CH_3CH_2CH_2CH_2CH_2CH_2$— | H | —$CH_2CH_2NHCO_2CH_3$ |
| 129 | $CH_3CH_2CH_2CH_2CH_2CH_2$— | H | —$CH_2CH_2NHC(O)CH_3$ |
| 130 | $CH_3CH_2CH_2CH_2CH_2CH_2$— | H | —$CH_2CH_2NHC(O)NHCH_3$ |
| 131 | $CH_3CH_2CH_2CH_2CH_2CH_2$— | H | —$CH_2NH$—$NHCO_2CH_3$ |
| 132 | $CH_3CH_2CH_2CH_2CH_2CH_2$— | H | —$CH_2NH$—$NHC(O)CH_3$ |
| 135 | $CH_3CH_2CH_2CH_2CH_2CH_2$ | $CH_3$ | —CH═CHNH—C(O)$CH_3$ |

TABLE 1-continued

Examples of Specific Compounds of Formula I

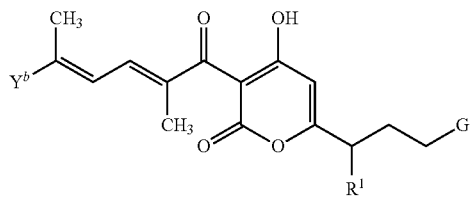

Examples of Specific Compounds of Formula I ($Y^a$ = $CH_3$ and $R^2$ = H)

| No. | $Y^b$ | $R^1$ | G |
| --- | --- | --- | --- |
| 136 | $CH_3CH_2CH_2CH_2CH_2CH_2$— | $CH_3$ | —CH=CHNH—C(O)$CH_2CH_3$ |
| 137 | $CH_3CH_2CH_2CH_2CH_2CH_2$— | $CH_3$ | —CH=CHNH—C(O)NH$CH_3$ |
| 138 | $CH_3CH_2CH_2CH_2CH_2CH_2$— | $CH_3$ | —CH=CHNH—C(S)O$CH_3$ |
| 139 | $CH_3CH_2CH_2CH_2CH_2CH_2$— | $CH_3$ | —$CH_2CH_2$NH$CO_2CH_3$ |
| 140 | $CH_3CH_2CH_2CH_2CH_2CH_2$— | $CH_3$ | —$CH_2CH_2$NHC(O)$CH_3$ |
| 141 | $CH_3CH_2CH_2CH_2CH_2CH_2$— | $CH_3$ | —$CH_2CH_2$NHC(O)NH$CH_3$ |
| 142 | $CH_3CH_2CH_2CH_2CH_2CH_2$— | $CH_3$ | —$CH_2$NH—NH$CO_2CH_3$ |
| 143 | $CH_3CH_2CH_2CH_2CH_2CH_2$— | $CH_3$ | —$CH_2$NH—NHC(O)$CH_3$ |
| 148 | $CH_3CH_2CH_2CH_2CH_2CH_2$— | H | —CH=CHNH—$CO_2CH_2CH_3$ |
| 149 | $CH_3CH_2CH_2CH_2CH_2CH_2$— | H | —CH=CHNH—C(O)$CH_3$ |
| 150 | $CH_3CH_2CH_2CH_2CH_2CH_2$— | H | —CH=CHNH—C(O)$CH_2CH_3$ |
| 151 | $CH_3CH_2CH_2CH_2CH_2CH_2$— | H | —CH=CHNH—C(O)NH$CH_3$ |
| 152 | $CH_3CH_2CH_2CH_2CH_2CH_2$— | H | —CH=CHNH—C(S)O$CH_3$ |
| 153 | $CH_3CH_2CH_2CH_2CH_2CH_2$— | H | —$CH_2CH_2$NH$CO_2CH_3$ |
| 154 | $CH_3CH_2CH_2CH_2CH_2CH_2$— | H | —$CH_2CH_2$NHC(O)$CH_3$ |
| 155 | $CH_3CH_2CH_2CH_2CH_2CH_2$— | H | —$CH_2CH_2$NHC(O)NH$CH_3$ |
| 156 | $CH_3CH_2CH_2CH_2CH_2CH_2$— | H | —$CH_2$NH—NH$CO_2CH_3$ |
| 157 | $CH_3CH_2CH_2CH_2CH_2CH_2$— | H | —$CH_2$NH—NHC(O)$CH_3$ |
| 158 | $CH_3CH_2CH_2CH_2CH_2CH_2$ | $CH_3$ | —CH=CHNH—$CO_2CH_3$ |
| 159 | $CH_3CH_2CH_2CH_2CH_2CH_2$— | $CH_3$ | —CH=CHNH—$CO_2CH_2CH_3$ |
| 160 | $CH_3CH_2CH_2CH_2CH_2CH_2$ | $CH_3$ | —CH=CHNH—C(O)$CH_3$ |
| 161 | $CH_3CH_2CH_2CH_2CH_2CH_2$— | $CH_3$ | —CH=CHNH—C(O)$CH_2CH_3$ |
| 162 | $CH_3CH_2CH_2CH_2CH_2CH_2$— | $CH_3$ | —CH=CHNH—C(O)NH$CH_3$ |
| 163 | $CH_3CH_2CH_2CH_2CH_2CH_2$— | $CH_3$ | —CH=CHNH—C(S)O$CH_3$ |
| 164 | $CH_3CH_2CH_2CH_2CH_2CH_2$— | $CH_3$ | —$CH_2CH_2$NH$CO_2CH_3$ |
| 165 | $CH_3CH_2CH_2CH_2CH_2CH_2$— | $CH_3$ | —$CH_2CH_2$NHC(O)$CH_3$ |
| 166 | $CH_3CH_2CH_2CH_2CH_2CH_2$— | $CH_3$ | —$CH_2CH_2$NHC(O)NH$CH_3$ |
| 167 | $CH_3CH_2CH_2CH_2CH_2CH_2$— | $CH_3$ | —$CH_2$NH—NH$CO_2CH_3$ |
| 168 | $CH_3CH_2CH_2CH_2CH_2CH_2$— | $CH_3$ | —$CH_2$NH—NHC(O)$CH_3$ |
| 170 | $CH_3CH_2CH_2CH_2CH_2CH_2CH_2$— | H | —CH=CHNH—$CO_2CH_2CH_3$ |
| 171 | $CH_3CH_2CH_2CH_2CH_2CH_2CH_2$ | H | —CH=CHNH—C(O)$CH_3$ |
| 172 | $CH_3CH_2CH_2CH_2CH_2CH_2CH_2$— | H | —CH=CHNH—C(O)$CH_2CH_3$ |
| 173 | $CH_3CH_2CH_2CH_2CH_2CH_2CH_2$— | H | —CH=CHNH—C(O)NH$CH_3$ |
| 174 | $CH_3CH_2CH_2CH_2CH_2CH_2CH_2$— | H | —CH=CHNH—C(S)O$CH_3$ |
| 175 | $CH_3CH_2CH_2CH_2CH_2CH_2CH_2$— | H | —$CH_2CH_2$NH$CO_2CH_3$ |
| 176 | $CH_3CH_2CH_2CH_2CH_2CH_2CH_2$— | H | —$CH_2CH_2$NHC(O)$CH_3$ |
| 177 | $CH_3CH_2CH_2CH_2CH_2CH_2CH_2$— | H | —$CH_2CH_2$NHC(O)NH$CH_3$ |
| 178 | $CH_3CH_2CH_2CH_2CH_2CH_2CH_2$— | H | —$CH_2$NH—NH$CO_2CH_3$ |
| 179 | $CH_3CH_2CH_2CH_2CH_2CH_2CH_2$— | H | —$CH_2$NH—NHC(O)$CH_3$ |
| 180 | $CH_3CH_2CH_2CH_2CH_2CH_2CH_2$ | $CH_3$ | —CH=CHNH—$CO_2CH_3$ |
| 181 | $CH_3CH_2CH_2CH_2CH_2CH_2CH_2$— | $CH_3$ | —CH=CHNH—$CO_2CH_2CH_3$ |
| 182 | $CH_3CH_2CH_2CH_2CH_2CH_2CH_2$ | $CH_3$ | —CH=CHNH—C(O)$CH_3$ |
| 183 | $CH_3CH_2CH_2CH_2CH_2CH_2CH_2$— | $CH_3$ | —CH=CHNH—C(O)$CH_2CH_3$ |
| 184 | $CH_3CH_2CH_2CH_2CH_2CH_2CH_2$— | $CH_3$ | —CH=CHNH—C(O)NH$CH_3$ |
| 185 | $CH_3CH_2CH_2CH_2CH_2CH_2CH_2$— | $CH_3$ | —CH=CHNH—C(S)O$CH_3$ |
| 186 | $CH_3CH_2CH_2CH_2CH_2CH_2CH_2$— | $CH_3$ | —$CH_2CH_2$NH$CO_2CH_3$ |
| 187 | $CH_3CH_2CH_2CH_2CH_2CH_2CH_2$— | $CH_3$ | —$CH_2CH_2$NHC(O)$CH_3$ |
| 188 | $CH_3CH_2CH_2CH_2CH_2CH_2CH_2$— | $CH_3$ | —$CH_2CH_2$NHC(O)NH$CH_3$ |
| 189 | $CH_3CH_2CH_2CH_2CH_2CH_2CH_2$— | $CH_3$ | —$CH_2$NH—NH$CO_2CH_3$ |
| 190 | $CH_3CH_2CH_2CH_2CH_2CH_2CH_2$— | $CH_3$ | —$CH_2$NH—NHC(O)$CH_3$ |
| 169 | $CH_3CH_2CH_2CH_2CH_2CH_2CH_2$ | H | —CH=CHNH—$CO_2CH_3$ |
| 170 | $(CH_3)_2CHCH_2CH_2CH_2CH_2$— | H | —CH=CHNH—$CO_2CH_2CH_3$ |
| 171 | $(CH_3)_2CHCH_2CH_2CH_2CH_2$— | H | —CH=CHNH—C(O)$CH_3$ |
| 172 | $(CH_3)_2CHCH_2CH_2CH_2CH_2$— | H | —CH=CHNH—C(O)$CH_2CH_3$ |
| 173 | $(CH_3)_2CHCH_2CH_2CH_2CH_2$— | H | —CH=CHNH—C(O)NH$CH_3$ |
| 174 | $(CH_3)_2CHCH_2CH_2CH_2CH_2$ | H | —CH=CHNH—C(S)O$CH_3$ |
| 175 | $(CH_3)_2CHCH_2CH_2CH_2CH_2$ | H | —$CH_2CH_2$NH$CO_2CH_3$ |
| 176 | $(CH_3)_2CHCH_2CH_2CH_2CH_2$ | H | —$CH_2CH_2$NHC(O)$CH_3$ |
| 177 | $(CH_3)_2CHCH_2CH_2CH_2CH_2$ | H | —$CH_2CH_2$NHC(O)NH$CH_3$ |
| 178 | $(CH_3)_2CHCH_2CH_2CH_2CH_2$ | H | —$CH_2$NH—NH$CO_2CH_3$ |
| 179 | $(CH_3)_2CHCH_2CH_2CH_2CH_2$ | H | —$CH_2$NH—NHC(O)$CH_3$ |
| 180 | $(CH_3)_2CHCH_2CH_2CH_2CH_2$ | $CH_3$ | —CH=CHNH—$CO_2CH_3$ |
| 181 | $(CH_3)_2CHCH_2CH_2CH_2CH_2$ | $CH_3$ | —CH=CHNH—$CO_2CH_2CH_3$ |
| 182 | $(CH_3)_2CHCH_2CH_2CH_2CH_2$ | $CH_3$ | —CH=CHNH—C(O)$CH_3$ |

TABLE 1-continued

Examples of Specific Compounds of Formula I

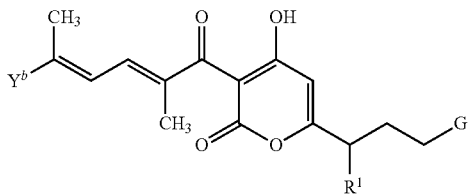

Examples of Specific Compounds of Formula I ($Y^a = CH_3$ and $R^2 = H$)

| No. | $Y^b$ | $R^1$ | G |
|---|---|---|---|
| 183 | $(CH_3)_2CHCH_2CH_2CH_2CH_2$ | $CH_3$ | —CH=CHNH—C(O)CH$_2$CH$_3$ |
| 184 | $(CH_3)_2CHCH_2CH_2CH_2CH_2$ | $CH_3$ | —CH=CHNH—C(O)NHCH$_3$ |
| 185 | $(CH_3)_2CHCH_2CH_2CH_2CH_2$ | $CH_3$ | —CH=CHNH—C(S)OCH$_3$ |
| 186 | $(CH_3)_2CHCH_2CH_2CH_2CH_2$ | $CH_3$ | —CH$_2$CH$_2$NHCO$_2$CH$_3$ |
| 187 | $(CH_3)_2CHCH_2CH_2CH_2CH_2$ | $CH_3$ | —CH$_2$CH$_2$NHC(O)CH$_3$ |
| 188 | $(CH_3)_2CHCH_2CH_2CH_2CH_2$ | $CH_3$ | —CH$_2$CH$_2$NHC(O)NHCH$_3$ |
| 189 | $(CH_3)_2CHCH_2CH_2CH_2CH_2$ | $CH_3$ | —CH$_2$NH—NHCO$_2$CH$_3$ |
| 190 | $(CH_3)_2CHCH_2CH_2CH_2CH_2$ | $CH_3$ | —CH$_2$NH—NHC(O)CH$_3$ |

TABLE 2

Examples of Specific Compounds of Formula I

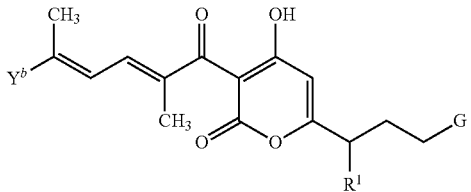

Examples of Specific Compounds of Formula I ($Y^a = CH_3$ and $R^2 = H$)

| No. | $Y^b$ | $R^1$ | G |
|---|---|---|---|
| 200 | $CH_3CH_2CH_2$— | $CH_3$ | —CH$_2$CH$_2$NHCO$_2$CH$_3$ |
| 201 | $CH_3CH_2CH_2$— | $CH_3$ | —CH$_2$CH$_2$NHC(O)CH$_3$ |
| 202 | $CH_3CH_2CH_2$— | $CH_3$ | —CH$_2$NH—NHC(O)NHCH$_3$ |
| 203 | $CH_3CH_2CH_2$— | $CH_3$ | —CH$_2$NH—NHCO$_2$CH$_3$ |
| 204 | $CH_3CH_2CH_2$— | $CH_3$ | —CH$_2$NH—NHCOCH$_3$ |
| 205 | $CH_3CH_2CH_2$— | H | —CH=CHNH—C(O)NHCH$_3$ |
| 206 | $CH_3CH_2CH_2$— | H | —CH$_2$CH$_2$NHCO$_2$CH$_3$ |
| 207 | $CH_3CH_2CH_2$— | H | —CH$_2$CH$_2$NHC(O)CH$_3$ |
| 208 | $CH_3CH_2CH_2$— | H | —CH$_2$CH$_2$NHC(S)OCH$_3$ |
| 209 | $CH_3CH_2CH_2$— | H | —CH$_2$NH—NHCO$_2$CH$_3$ |
| 210 | $CH_3CH_2CH_2$— | H | —CH$_2$NH—NHCOCH$_3$ |
| 211 | $CH_3CH_2CH_2CH_2$— | H | —CH$_2$CH$_2$NHCO$_2$CH$_3$ |
| 212 | $CH_3CH_2CH_2CH_2$— | $CH_3$ | —CH$_2$CH$_2$NHC(O)CH$_3$ |
| 213 | $CH_3CH_2CH_2CH_2$— | $CH_3$ | —CH$_2$NH—NHC(O)NHCH$_3$ |
| 214 | $CH_3CH_2CH_2CH_2$— | $CH_3$ | —CH$_2$NH—NHCO$_2$CH$_3$ |
| 215 | $CH_3CH_2CH_2CH_2$— | $CH_3$ | —CH$_2$NH—NHCOCH$_3$ |
| 216 | $CH_3CH_2CH_2CH_2$— | H | —CH$_2$CH$_2$NHCO$_2$CH$_3$ |
| 217 | $CH_3CH_2CH_2CH_2$— | H | —CH$_2$CH$_2$NHC(O)CH$_3$ |
| 218 | $CH_3CH_2CH_2CH_2$— | H | —CH=CHNH—C(O)NHCH$_3$ |
| 219 | $CH_3CH_2CH_2CH_2$— | H | —CH$_2$NH—NHCO$_2$CH$_3$ |
| 220 | $CH_3CH_2CH_2CH_2$— | H | —CH$_2$NH—NHCOCH$_3$ |
| 221 | $(CH_3)_2C$=CHCH$_2$CH$_2$— | H | —CH=CHNHCO$_2$CH$_3$ |
| 222 | $(CH_3)_2C$=CHCH$_2$CH$_2$— | $CH_3$ | —CH=CHNHC(O)CH$_3$ |
| 223 | $(CH_3)_2C$=CHCH$_2$CH$_2$— | H | —CH=CHNHCO$_2$CH$_3$ |
| 224 | $(CH_3)_2C$=CHCH$_2$CH$_2$— | H | —CH=CHNHC(O)CH$_3$ |
| 225 | $(CH_3)_2C$=CHCH$_2$CH$_2$— | $CH_3$ | —CH$_2$CH$_2$NHCO$_2$CH$_3$ |
| 226 | $(CH_3)_2C$=CHCH$_2$CH$_2$— | $CH_3$ | —CH$_2$CH$_2$NHC(O)CH$_3$ |
| 227 | $(CH_3)_2C$=CHCH$_2$CH$_2$— | $CH_3$ | —CH=CHNH—C(O)NHCH$_3$ |
| 228 | $(CH_3)_2C$=CHCH$_2$CH$_2$— | $CH_3$ | —CH$_2$NH—NHCO$_2$CH$_3$ |
| 229 | $(CH_3)_2C$=CHCH$_2$CH$_2$— | $CH_3$ | —CH$_2$NH—NHCOCH$_3$ |
| 230 | $(CH_3)_2C$=CHCH$_2$CH$_2$— | H | —CH$_2$CH$_2$NHCO$_2$CH$_3$ |
| 231 | $(CH_3)_2C$=CHCH$_2$CH$_2$— | H | —CH$_2$CH$_2$NHC(O)CH$_3$ |

TABLE 2-continued

Examples of Specific Compounds of Formula I

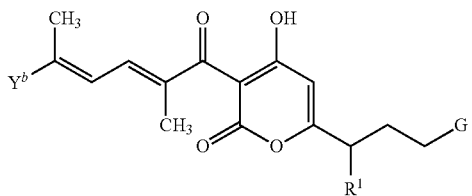

Examples of Specific Compounds of Formula I ($Y^a$ = $CH_3$ and $R^2$ = H)

| No. | $Y^b$ | $R^1$ | G |
|---|---|---|---|
| 232 | $(CH_3)_2C$=$CHCH_2CH_2$— | H | —$CH_2CH_2NHC(S)OCH_3$ |
| 233 | $(CH_3)_2C$=$CHCH_2CH_2$— | H | —$CH_2NH$—$NHCO_2CH_3$ |
| 234 | $(CH_3)_2C$=$CHCH_2CH_2$— | H | —$CH_2NH$—$NHCOCH_3$ |
| 235 | $(CH_3)_2C$=$CHCH_2CH_2$— | $CH_3$ | —$CH_2NH$—$NHC(O)NHCH_3$ |
| 236 | $(CH_3)_2C$=$CHCH_2CH_2$— | $CH_3$ | —$CH$=$CHNHC(O)CH_2CH_3$ |
| 237 | $CH_3$—$CH$=$CHCH_2CH$=$C(CH_3)CH(OH)CH_2CH_2$— | H | —$CH$=$CHNHC(O)CH_3$ |
| 238 | $CH_3$—$CH$=$CHCH_2CH$=$C(CH_3)CH(OH)CH_2CH_2$— | H | —$CH$=$CHNHCO_2CH_3$ |
| 239 | $CH_3$—$CH$=$CHCH_2CH$=$C(CH_3)CH(OH)CH_2CH_2$— | $CH_3$ | —$CH$=$CHNHC(O)CH_3$ |
| 240 | $CH_3$—$CH$=$CHCH_2CH$=$C(CH_3)CH(OH)CH_2CH_2$— | $CH_3$ | —$CH_2CH_2NHCO_2CH_3$ |
| 241 | $CH_3$—$CH$=$CHCH_2CH$=$C(CH_3)CH(OH)CH_2CH_2$— | $CH_3$ | —$CH_2CH_2NHC(O)CH_3$ |
| 242 | $CH_3$—$CH$=$CHCH_2CH$=$C(CH_3)CH(OH)CH_2CH_2$— | $CH_3$ | —$CH$=$CHNH$—$C(O)NHCH_3$ |
| 243 | $CH_3$—$CH$=$CHCH_2CH$=$C(CH_3)CH(OH)CH_2CH_2$— | $CH_3$ | —$CH_2NH$—$NHCO_2CH_3$ |
| 247 | $CH_3$—$CH$=$CHCH_2CH$=$C(CH_3)CH(OH)CH_2CH_2$— | H | —$CH_2NH$—$NHCOCH_3$ |
| 248 | $CH_3$—$CH$=$CHCH_2CH$=$C(CH_3)CH(OH)CH_2CH_2$— | H | —$CH_2CH_2NHCO_2CH_3$ |
| 249 | $CH_3$—$CH$=$CHCH_2CH$=$C(CH_3)CH(OH)CH_2CH_2$— | H | —$CH_2CH_2NHC(O)CH_3$ |
| 250 | $CH_3$—$CH$=$CHCH_2CH$=$C(CH_3)CH(OH)CH_2CH_2$— | H | —$CH_2NH$—$NHC(O)NHCH_3$ |
| 251 | $CH_3$—$CH$=$CHCH_2CH$=$C(CH_3)CH(OH)CH_2CH_2$— | H | —$CH_2NH$—$NHCO_2CH_3$ |
| 252 | $CH_3$—$CH$=$CHCH_2CH$=$C(CH_3)CH(OH)CH_2CH_2$— | $CH_3$ | —$CH_2NH$—$NHCOCH_3$ |
| 253 | $CH_3$—$CH$=$CHCH_2CH$=$C(CH_3)CH(OH)CH_2CH_2$— | $CH_3$ | —$CH$=$CHNHCO_2CH_2CH_3$ |
| 254 | $CH_2$=$C(CH_3)CH(OH)CH_2CH_2$— | H | —$CH$=$CHNHC(O)CH_3$ |
| 255 | $CH_2$=$C(CH_3)CH(OH)CH_2CH_2$— | H | —$CH$=$CHNHCO_2CH_3$ |
| 256 | $CH_2$=$C(CH_3)CH(OH)CH_2CH_2$— | $CH_3$ | —$CH$=$CHNHC(O)CH_3$ |
| 257 | $CH_2$=$C(CH_3)CH(OH)CH_2CH_2$— | $CH_3$ | —$CH_2CH_2NHCO_2CH_3$ |
| 258 | $CH_2$=$C(CH_3)CH(OH)CH_2CH_2$— | $CH_3$ | —$CH_2CH_2NHC(O)CH_3$ |
| 259 | $CH_2$=$C(CH_3)CH(OH)CH_2CH_2$— | $CH_3$ | —$CH$=$CHNH$—$C(O)NHCH_3$ |
| 260 | $CH_2$=$C(CH_3)CH(OH)CH_2CH_2$— | $CH_3$ | —$CH_2NH$—$NHCO_2CH_3$ |
| 261 | $CH_2$=$C(CH_3)CH(OH)CH_2CH_2$— | H | —$CH_2NH$—$NHCOCH_3$ |
| 262 | $CH_2$=$C(CH_3)CH(OH)CH_2CH_2$— | H | —$CH_2CH_2NHCO_2CH_3$ |
| 263 | $CH_2$=$C(CH_3)CH(OH)CH_2CH_2$— | H | —$CH_2CH_2NHC(O)CH_3$ |
| 264 | $CH_2$=$C(CH_3)CH(OH)CH_2CH_2$— | H | —$CH_2NH$—$NHC(O)NHCH_3$ |
| 265 | $CH_2$=$C(CH_3)CH(OH)CH_2CH_2$— | H | —$CH_2NH$—$NHCO_2CH_3$ |
| 266 | $CH_2$=$C(CH_3)CH(OH)CH_2CH_2$— | $CH_3$ | —$CH_2NH$—$NHCOCH_3$ |
| 267 | $CH_2$=$C(CH_3)CH(OH)CH_2CH_2$— | $CH_3$ | —$CH$=$CHNHCO_2CH_2CH_3$ |

In another embodiment, $Y^a$ and $Y^b$ are identical $C_1$-$C_3$ alkyl, and $R^1$, $R^2$, and G are as described above. Other examples of this embodiment include the following:

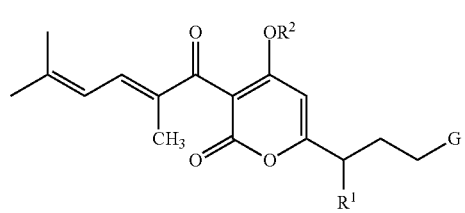

268

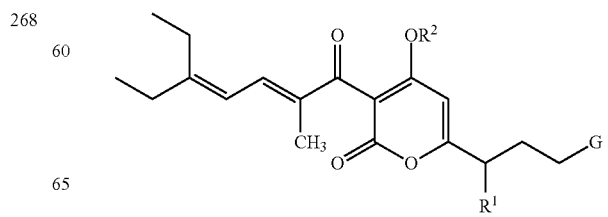

269

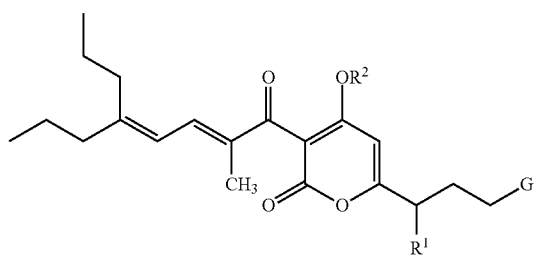
270

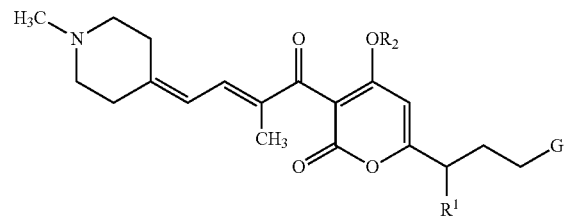
274

In another embodiment, $Y^a$ and $Y^b$ are taken together with their intervening atom to form a 4-6 membered ring having 0-1 heteroatoms selected from nitrogen, oxygen or sulfur. For example, $Y^a$ and $Y^b$ may taken together with their intervening atom to form a cyclopentyl or cyclohexyl ring where $R^1$, $R^2$, and G are as described above. Other examples of this embodiment include the following:

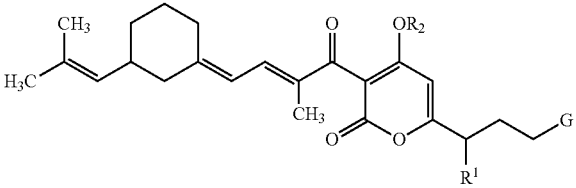
275

271

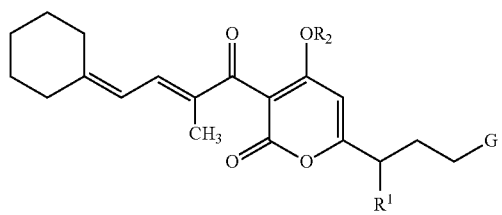

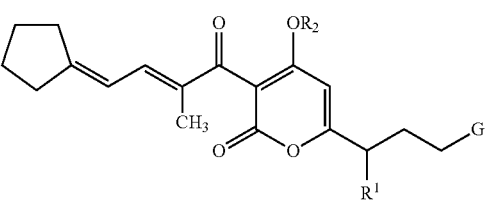
276

272

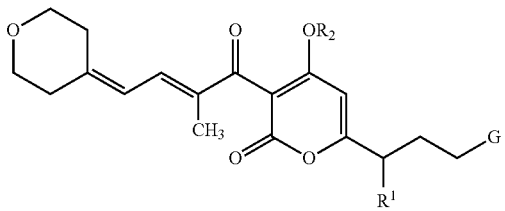

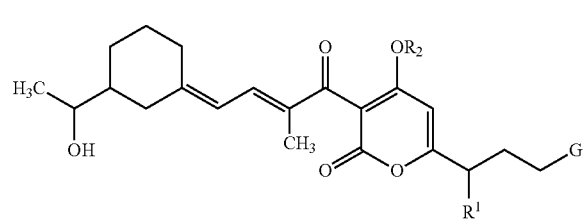
273

277 where $R^1$, $R^2$, and G are as described above.

In one specific embodiment the invention provides the compound:

XI

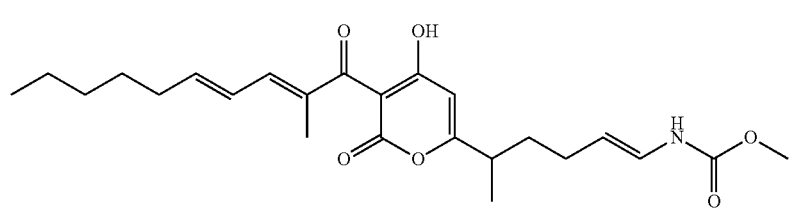

-continued
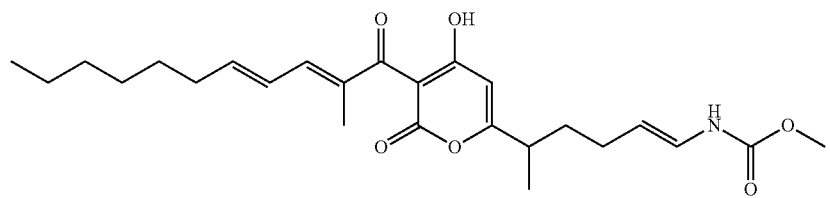
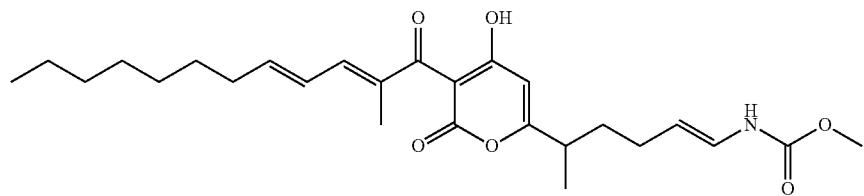
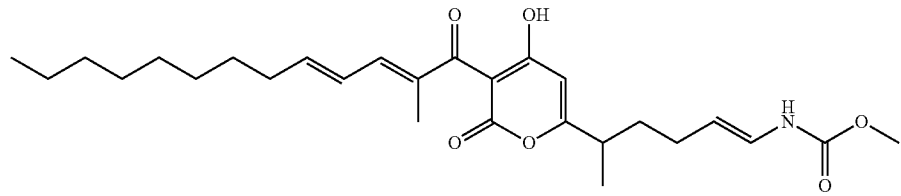
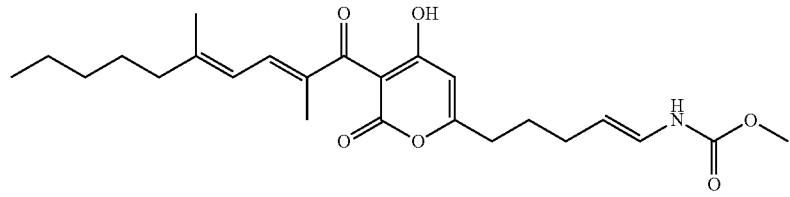
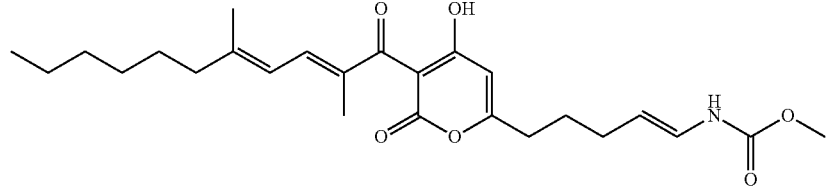
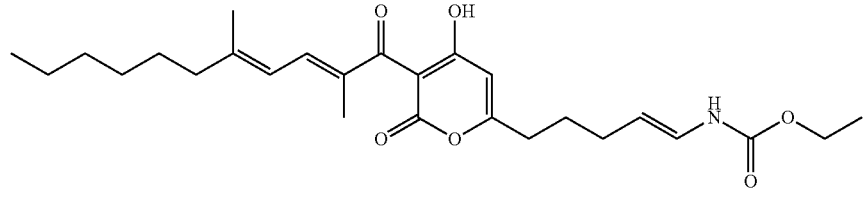
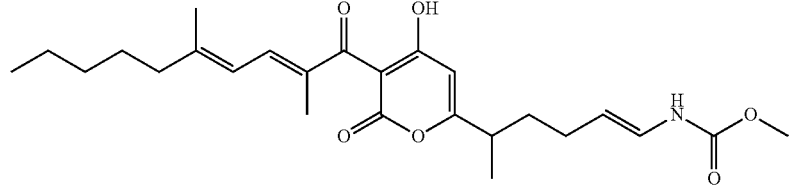
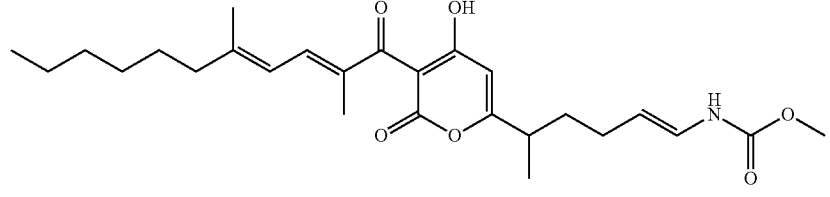

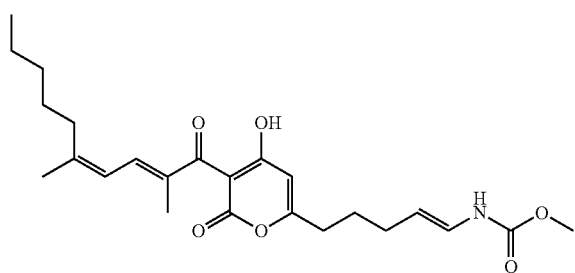
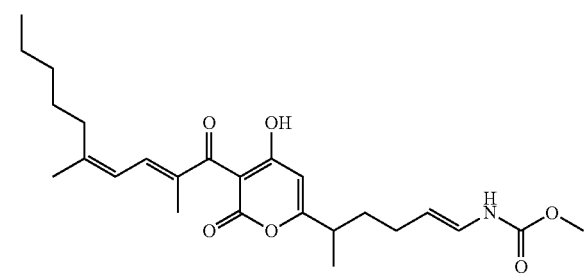

or a salt thereof.

Compound Synthesis

Compounds of Formula I may be prepared by the synthetic schemes (1-4) shown below, and by reference to analogous chemistry known in the art as well as synthetic examples presented herein. Useful literature references are those that describe the synthesis of other alpha-pyrone compounds. See Lira, R. et al., (2007) Bioorg. Med. Chem. Letters 17, 6797-6800; Doundoulakis, T. et al. (2004), Bioorg. Med. Chem. Letters 14, 5667-5672; Xiang, A. X. et al. (2006), Heterocycles 68, 1099-1103; Wardenga, G., (2007) Enwicklung eines synthetischen Zugangs zu potentiellen Antibiotika auf Basis der Naturstoffs Corallopyronin A. Thesis, (Gottfried Wilhelm Leibniz Universität, Hannover, Germany); and U.S. Pat. Nos. 6,239,291; 6,191,288, and 6,022,983.

Scheme 1 General Scheme for Preparing Certain Compounds of Formula I

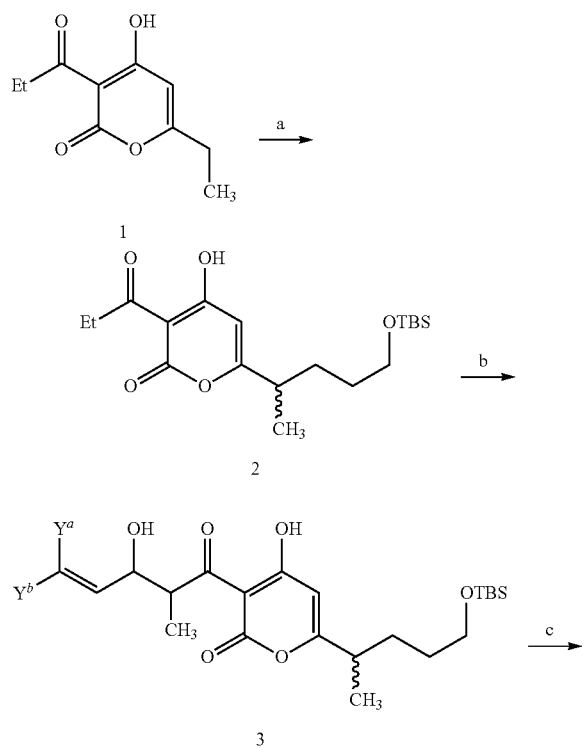

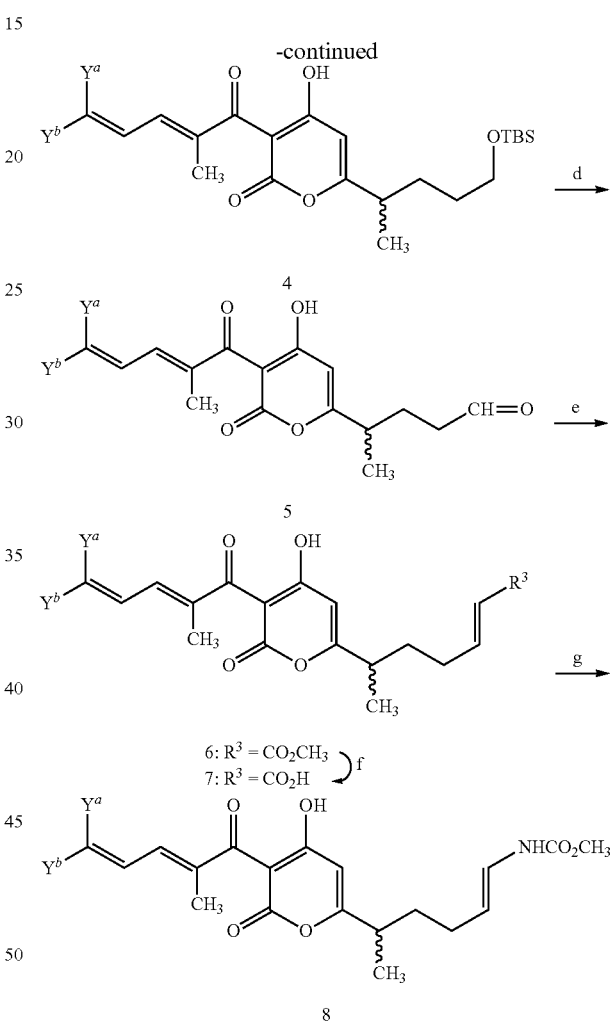

Reagents and conditions: (a) I(CH$_2$)$_3$OTBS, LDA (3.2 eq), THF/HMPA, −78° C.; (b) LDA (2.1 eq), THF, −78° C., OHC—CH═C(Y$^a$)(Y$^b$); (c) (1) MsCl, TEA, then (2) DBU, THF, −78° C.; (d) (1) AcOH, H$_2$O, THF, then (2) DMSO, (COCl)$_2$, TEA; (e) NaH, (MeO)$_2$P(O)CH$_2$CO$_2$Me; (f) LiOH, THF; (g) (1) ethyl chloroformate, diisopropylethylamine, NaN$_3$, then (2) toluene, MeOH, reflux.

Scheme 1 above shows a general route for preparing certain compounds of formula I. The scheme is illustrated for compounds where R$^1$ is —CH$_3$, L is —CH$_2$CH$_2$—, G is —CH═CH—R$^3$ and R$^3$ is either CO$_2$CH$_3$ or CO$_2$H. One skilled in the art will understand how the general scheme may be modified in various ways to obtain other compounds of Formula I. For example, the silyl-protected iodopropanol used in step (a) may be replaced by longer or shorter silyl-protected iodo-alcohols to obtain compounds with different length L moieties. Furthermore, one skilled in the art will appreciate that compounds 4, 5, 6, 7 and 8 in Scheme 1 are useful intermediates for obtaining further compounds of Formula I by methods that are well-known in the art.

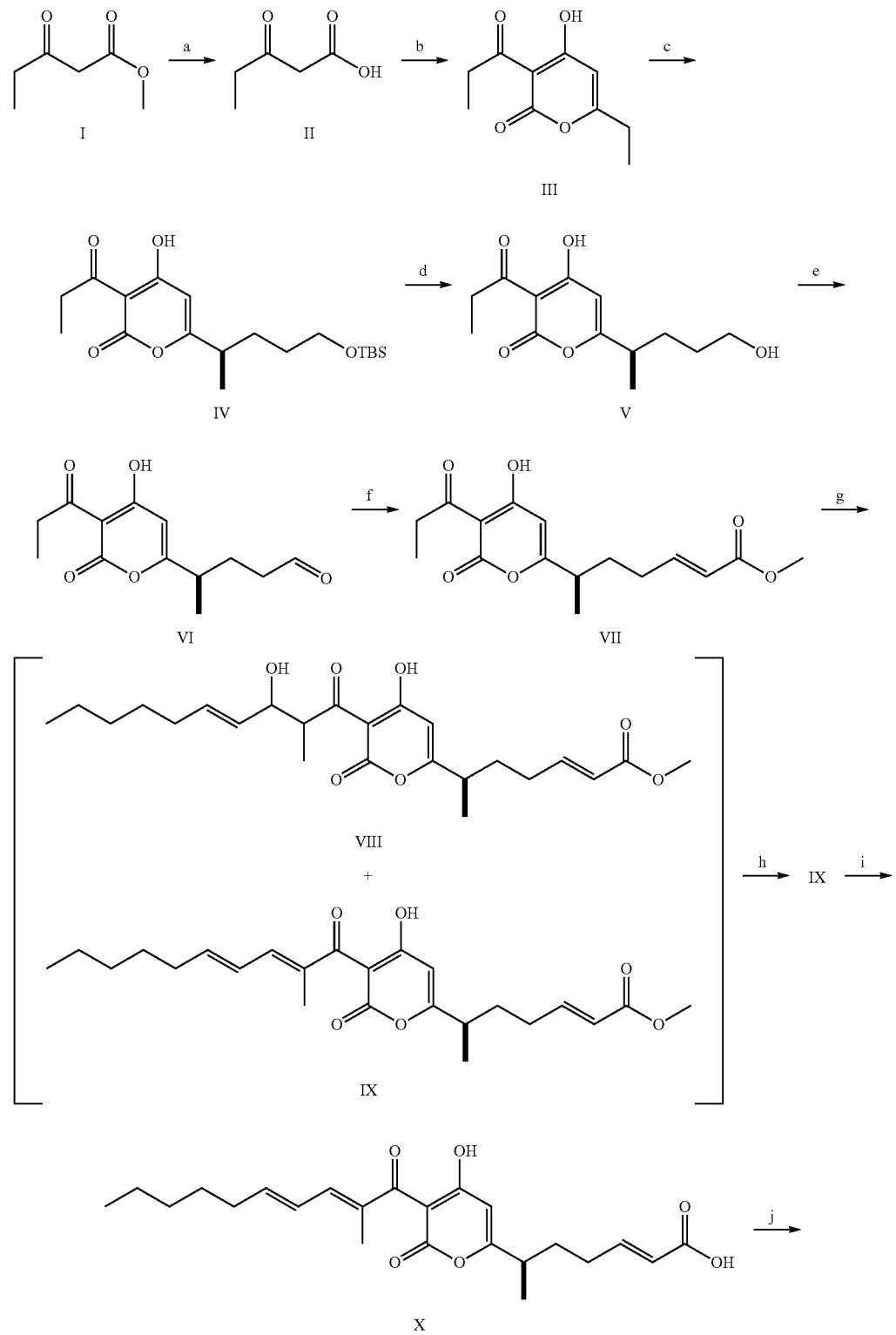

Scheme 2

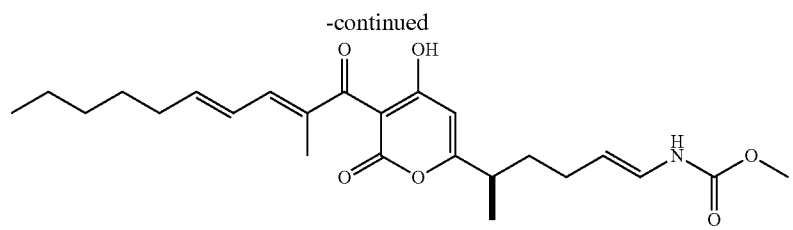
XI
a = NaOH; b = CDI; c = LDA, Br—Pr—OTBS; d = AcOH, THF, H₂O; e = sodium periodinate, pyridine; f = NaH, trimethyl phosphonoacetate; g = TiCl₄, DIPEA, trans 2-octenal;
h = p-toluene sulfonic acid, benzene; i = LiOH; j = (1) EtOCOCl, DIPEA, NaN₃; (2) toluene extraction; (3) toluene/MeOH reflux
Scheme 3
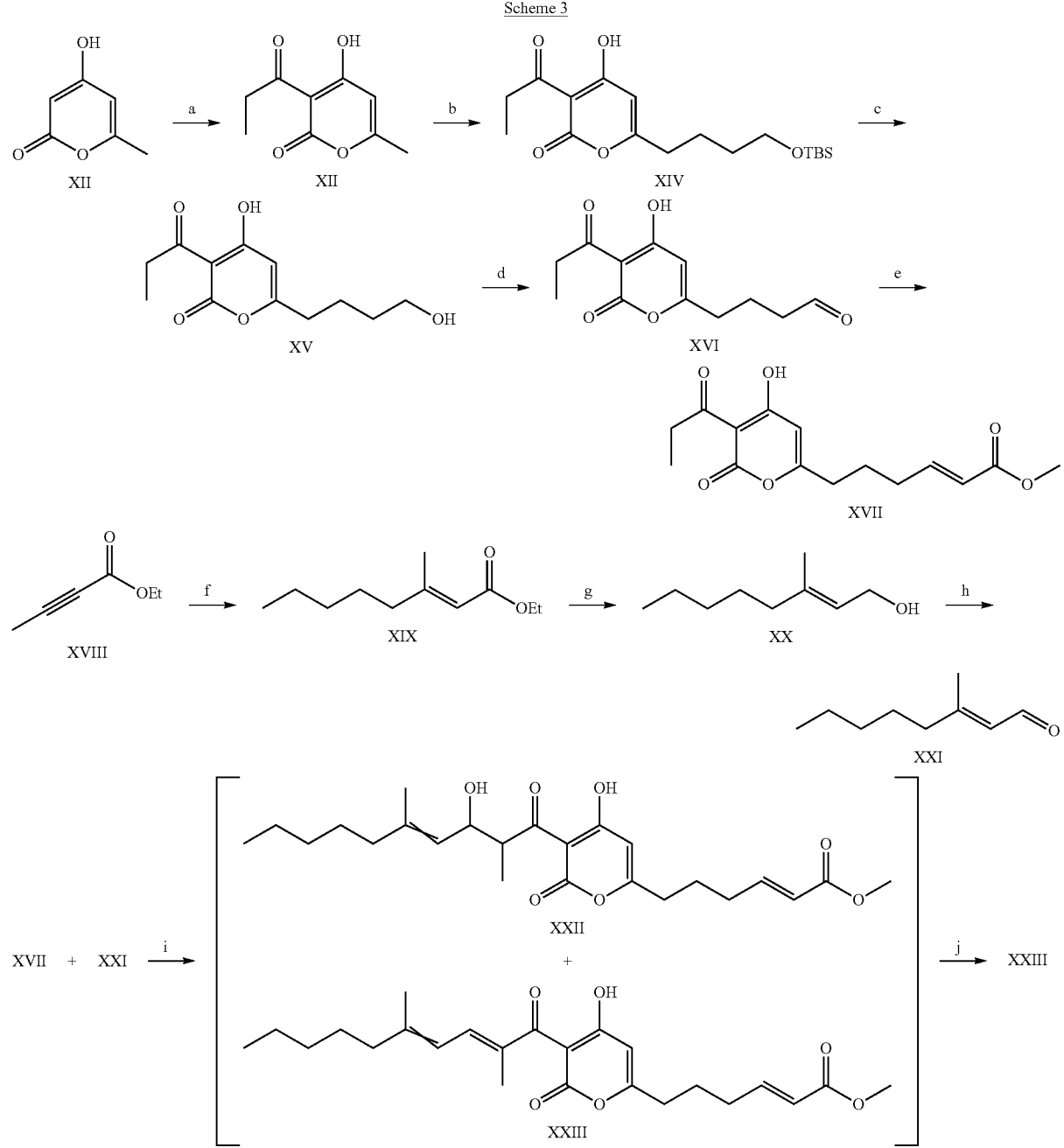

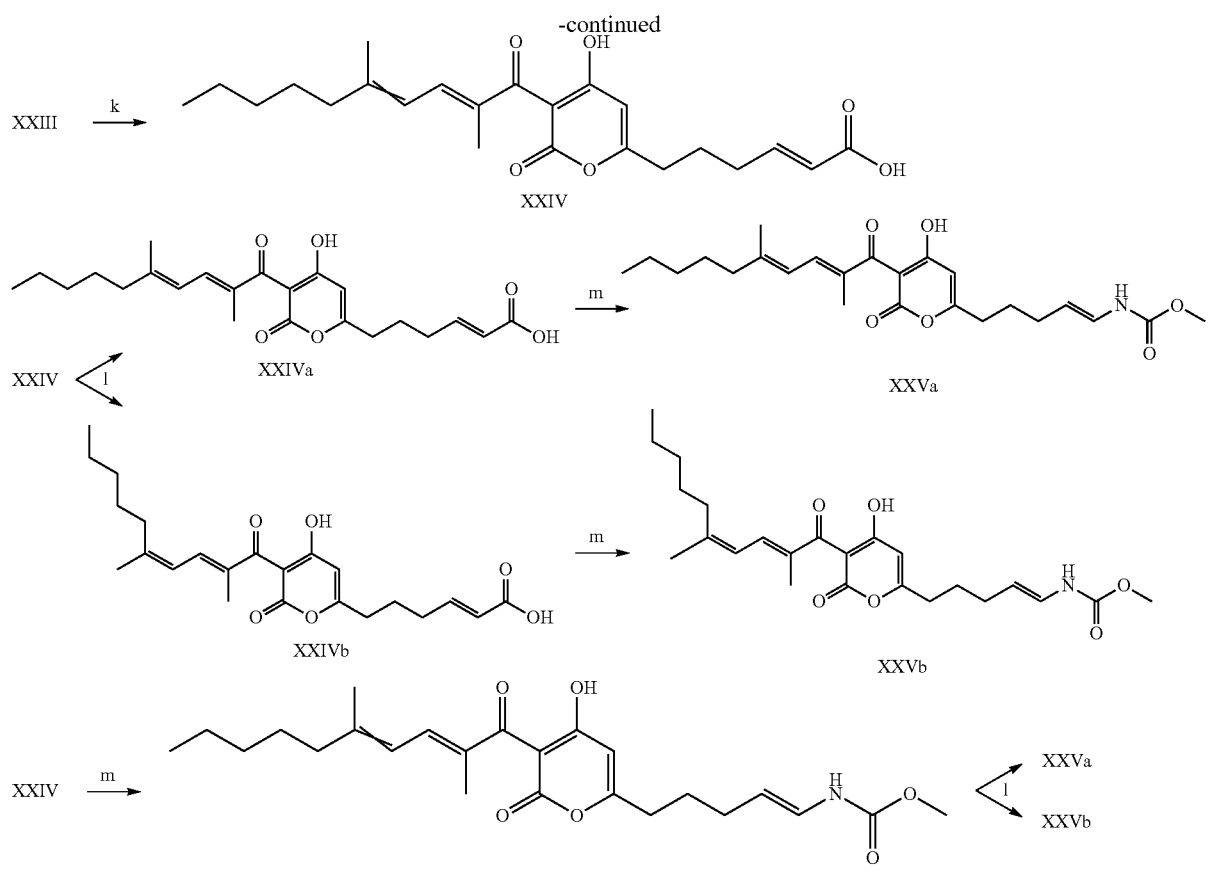
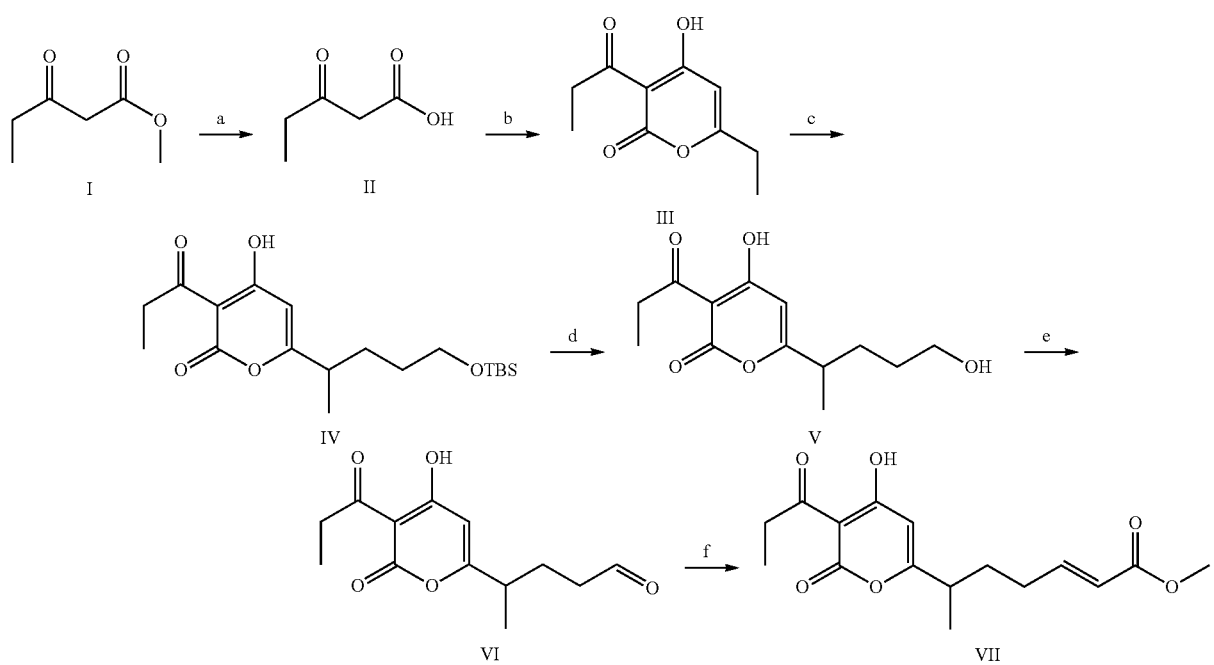
a = CH₃CH₂CO₂H, TEA, DCC, DMAP; b = LDA, Br—Pr—OTBS; c = AcOH, THF, H₂O; d = sodium periodinate, pyridine; e = NaH, trimethyl phosphonoacetate; f = CuI, n-pentyllithium; g = DIBAH; h = TPAP/NMO; i = TiCl₄, DIPEA; j = p-toluene sulfonic acid, benzene; k = LiOH; l = RP—HPLC; m = (1) EtOCOCl, DIPEA, NaN₃; (2) toluene extraction; (3) toluene/MeOH reflux
Scheme 4

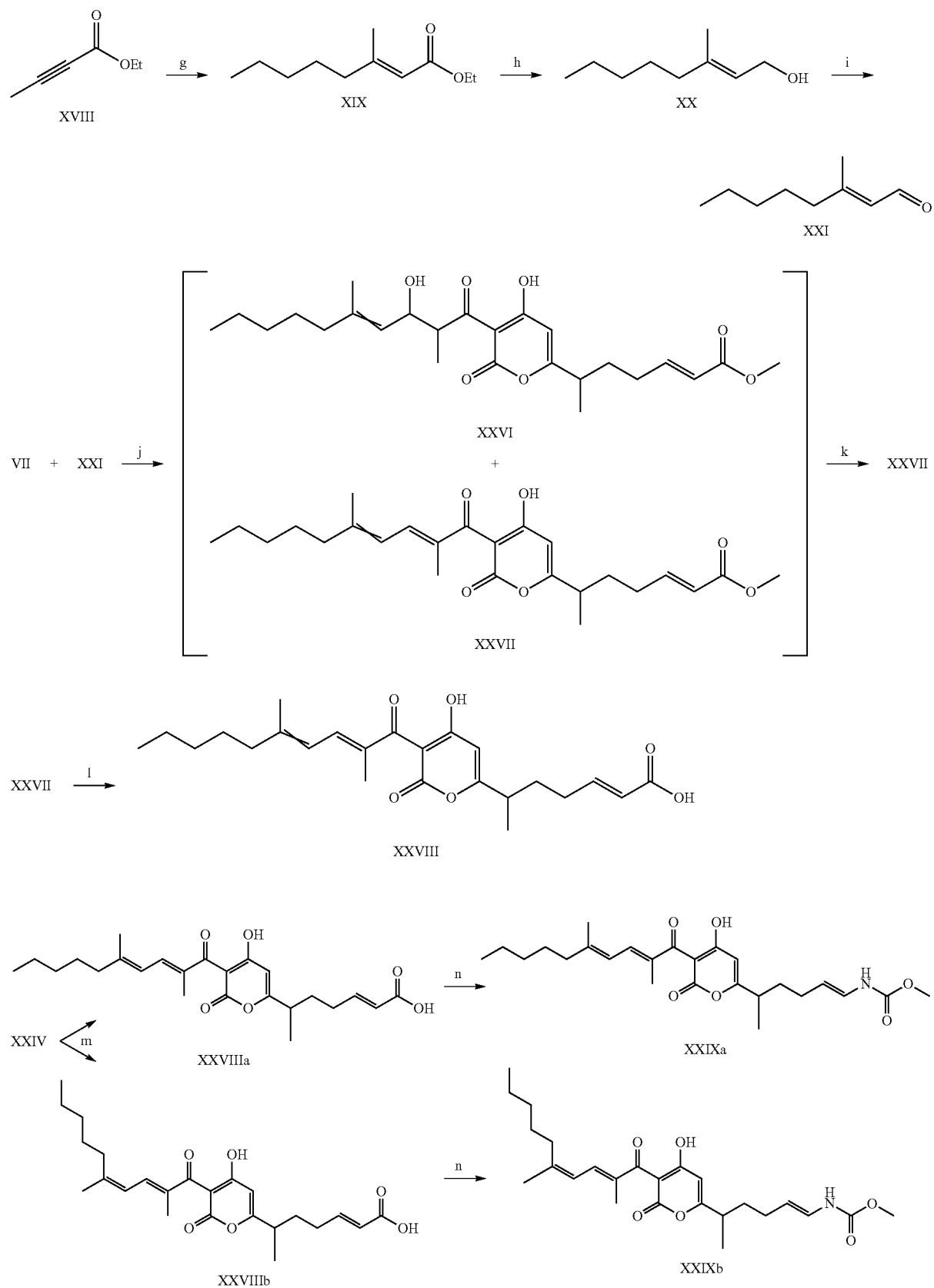

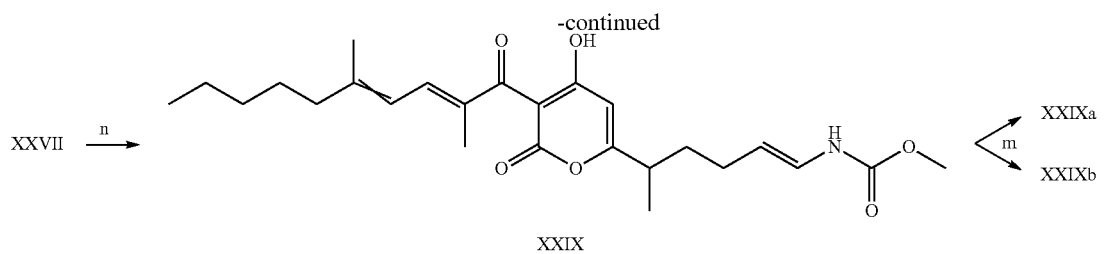

XXVII $\xrightarrow{n}$

XXIX $\begin{matrix} \nearrow \text{XXIXa} \\ \xleftarrow{m} \\ \searrow \text{XXIXb} \end{matrix}$ a = NaOH; b = CDI; c = LDA, Br—Pr—OTBS; d = AcOH, THF, H₂O; e = sodium periodinate, pyridine; f = NaH, trimethyl phosphonoacetate; g = CuI, n-pentyllithium; h = DIBAH; i = TPAP/NMO; j = TiCl₄, DIPEA; k = p-toluene sulfonic acid, benzene; l = LiOH; m = RP—HPLC; n = (1) EtOCOCl, DIPEA, NaN₃; (2) toluene extraction; (3) toluene/MeOH reflux In Schemes 3 and 4 above, a crossed-double-bond symbol denotes an unspecified double-bond configuration (i.e., a mixture of E configuration and Z configuration).

Uses

The invention provides a method for inhibiting the growth of a bacterium, comprising contacting the bacterium with a compound of Formula I or a salt thereof.

One embodiment of this invention relates to a method of treating a bacterial infection in a mammal, comprising administering to the mammal a therapeutically effective amount of a compound of Formula I or a pharmaceutically acceptable salt thereof.

In one aspect, the invention relates to a method for treating an infection associated with *Mycobacterium tuberculosis*, *Mycobacterium avium*, *Staphylococcus aureus*, *Enterococcus faecalis*, *Enterococcus faecium*, *Streptococcus pneumoniae*, *Enterobacter cloacae*, *Clostridium difficile*, *Acinetobacter baumannii*, or *Escherichia coli*.

Another embodiment of the invention relates to a method of preventing or reducing the risk of a bacterial infection in a patient, comprising administering to the patient a prophylactically effective amount of a compound of Formula I or a pharmaceutically acceptable salt thereof One aspect of the invention relates to a method of preventing or reducing the risk of a bacterial infection associated with *Mycobacterium tuberculosis, Mycobacterium avium, Staphylococcus aureus, Enterococcus faecalis, Enterococcus faecium, Streptococcus pneumoniae, Enterobacter cloacae*, or *Clostridium difficile, Acinetobacter baumannii*, or *Escherichia coli*.

The invention also provides the use of a compound of Formula I, or a pharmaceutically acceptable salt thereof, for the preparation of a medicament for treating or preventing a bacterial infection in a mammal.

The invention also provides the use of a compound of formula I, or a salt thereof, as a disinfectant, sterilant, antispoilant, or antiseptic.

The invention provides a method for inhibiting a bacterial RNAP, comprising contacting the bacterial RNAP with a compound of Formula I or a salt thereof.

The invention also provides the use of a compound of formula I, or a salt thereof, as a inhibitor or a bacterial RNAP.

The ability of a compound of the invention to inhibit a bacterial RNA polymerase, to inhibit bacterial growth in culture, and to inhibit bacterial growth in an animal can be determined using biochemical and microbiological models that are well known to the art, or as described in the Examples.

Administration of Pharmaceutical Compositions

The compounds of Formula I may be formulated as pharmaceutical compositions and administered to a mammalian host, such as a human patient in a variety of forms adapted to the chosen route of administration (i.e., orally or parenterally, by intravenous, intramuscular, topical or subcutaneous routes).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 125 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following illustrate representative preferred pharmaceutical dosage forms, containing a compound of formula I, or a pharmaceutically acceptable salt thereof, ('Compound X'), for therapeutic or prophylactic use in humans:

a) A formulation comprising from about 0.25 mg/ml to about 5 mg/ml of Compound X, about 5% to about 20% dimethylacetamide, and about 4% to about 16% Cremophor EL;

b) A formulation comprising from about 0.5 mg/ml to about 3 mg/ml of Compound X, about 5% to about 15% dimethylacetamide, and about 4% to about 12% Cremophor EL;

c) A formulation comprising about 2 mg/ml of Compound X, about 9% dimethylacetamide, and about 8% Cremophor EL.

In one embodiment of the invention, Compound X in the above formulations is a compound of formula 1a:

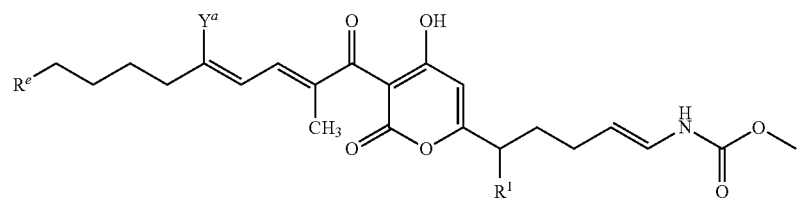

wherein: $R^e$ is H, methyl, or ethyl, which methyl or ethyl optionally is substituted with hydroxy, alkoxy, or halogen; $Y^a$ is H or methyl; and $R^1$ is H or methyl.

The invention will now be illustrated by the following non-limiting Examples.

EXAMPLES

Example 1

Methyl ((E)-5-(4-hydroxy-3-((2E,4E)-2-methyldeca-2,4-dienoyl)-2-oxo-2H-pyran-6-yl)hex-1-en-1-yl) carbamate (compound 1; XI in Scheme 2)

1

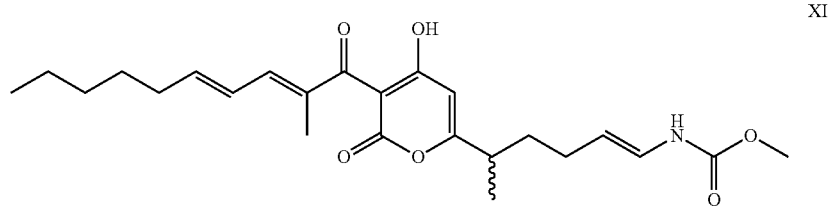

3-Oxopentanoic acid (II in Scheme 2)

Methyl propionylacetate (I; 10 g; 769 mmol; Aldrich) was stirred in 60 ml 1.5 M NaOH for 24 h at 25° C. The reaction mixture was diluted with 60 ml ice water, acidified with 3N HCl to pH 2, and solid KCl was added to saturation. The reaction mixture was extracted with 5×50 ml EtOAc, and the organic layers were pooled, dried with anhydrous $Na_2SO_4$, and evaporated to a white solid.

Yield: 8.9 g, 95%.

6-Ethyl-4-hydroxy-3-propionyl-2-H-pyran-2-one (III in Scheme 2)

3-Oxopentanoic acid (II; 2 g; 17.2 mmol) was dissolved in 30 ml THF and cooled to 0° C. To the solution, was added dicarbodiimidazole (3.6 g; 22.2 mmol; Aldrich). The reaction mixture was stirred for 18 h at 25° C., neutralized with 2% HCl, extracted with 3×30 ml EtOAc, dried with anhydrous $Na_2SO_4$, and evaporated to a white solid. The product was purified via silica chromatography (20% EtOAc in hexanes).

Yield: 1.3 g, 77%.

$^1$H-NMR (400 MHz, $CDCl_3$): δ 1.09 (t, 3H), 1.11 (t, 3H), 2.46 (q, 2H), 3.05 (q, 2H), 5.86 (s, 1H).

6-(5-(t-Butyldimethylsilyloxy)pentan-2-yl)-4-hydroxy-3-propionyl-2-H-pyran-2-one (IV in Scheme 2)

6-Ethyl-4-hydroxy-3-propionyl-2-H-pyran-2-one (III; 0.5 g; 2.56 mmol) was dissolved in 20 ml anhydrous THF and cooled to 0° C. under argon. To the cooled solution, was added LDA (5.12 ml of 1.5 M in cyclohexane; 7.68 mmol; Aldrich) and the reaction mixture was stirred for 30 min. To the cooled reaction mixture, was added 3-bromopropoxy-t-butyldimethylsilane (0.77 g; 3.07 mmol; Aldrich) and 1 ml HMPA (Aldrich). The reaction mixture was stirred for 30 min at 0° C., quenched with saturated $NH_4Cl$, extracted with 3×20 ml EtOAc, dried with anhydrous $Na_2SO_4$, and evaporated to an oil. The product was purified via silica chromatography (10% EtOAc in hexanes).

Yield: 0.588 g, 62.5%.

$^1$H-NMR (400 MHz, $CDCl_3$): δ 0 (s, 6H), 0.82 (s, 9H), 1.18 (t, 3H), 1.22 (d, 3H), 1.60 (m, 2H) 1.75 (m, 2H), 2.58 (m, 1H), 3.05 (q; 2H), 3.58 (t, 2H), 5.86 (s, 1H).

4-(5-Hydroxy-2-oxo-3-propionyl-2-H-pyran-6-yl) pentanol (V in Scheme 2)

6-(5-(t-Butyldimethylsilyloxy)pentan-2-yl)-4-hydroxy-3-propionyl-2-H-pyran-2-one (IV; 3 g; 8.15 mmol) in 100 ml AcOH/THF/water (3/1/1, v/v/v) was stirred for 18 h at 25° C. The reaction mixture was neutralized with saturated $NaHCO_3$, extracted with 3×50 ml EtOAc, dried with anhydrous $Na_2SO_4$, and evaporated to an oil. The product was purified via silica chromatography (40% EtOAc in hexanes).

Yield: 1.05 g, 53%.

$^1$H-NMR (400 MHz, $CDCl_3$): δ 1.18 (t, 2H), 1.22 (d, 3H), 1.60 (m, 2H) 1.75 (m, 2H), 2.58 (m, 1H), 3.05 (q; 2H), 3.62 (t, 2H), 5.86 (s, 1H).

4-(5-Hydroxy-2-oxo-3-propionyl-2-H-pyran-6-yl) pentanal (VI in Scheme 2)

4-(5-Hydroxy-2-oxo-3-propionyl-2-H-pyran-6-yl)pentanol (V; 0.38 g; 1.5 mmol; Aldrich) was dissolved in 20 ml dichloromethane and 0.6 ml pyridine. Sodium periodinate (0.7 g; 1.65 mmol; Aldrich) was added and stirred for 2 h at 25° C., after which reaction mixture was neutralized with saturated $NaHCO_3$ and extracted with 3×20 ml $CH_2Cl_2$. The pooled organic extracts were dried with anhydrous $Na_2SO_4$, evaporated, and purified via silica chromatography (20% EtOAc in hexanes).

Yield: 0.124 g, 33.3%.

$^1$H-NMR (400 MHz, $CDCl_3$): δ 1.18 (t, 3H), 1.26 (d, 3H), 1.90 (m, 1H), 2.05 (m, 1H), 2.50 (t, 2H), 2.62 (q, 1H), 3.10 (q, 2 μl), 5.95 (s; 1H), 9.80 (s, 1H).

(E)-Methyl 6-(4-hydroxy-2-oxo-3-propionyl-2-H-pyran-6-yl)hept-2-enoate (VII in Scheme 2)

NaH (0.06 g; 1.5 mmol; 60% dispersion in mineral oil; Aldrich) was added to trimethyl phosphonoacetate (0.190 g; 1.0 mmol; Aldrich) in 10 ml THF. The reaction mixture was stirred at 25° C. for 15 min, after which 4-(4-hydroxy-2-oxo-3-propionyl-2H-pyran-6-yl)pentanal (VI; 0.124 g; 0.5 mmol) in 10 ml THF was added. The reaction mixture was stirred at 25° C. for 4 h, quenched with saturated $NH_4Cl$, extracted with 3×20 ml EtOAc, dried with anhydrous $Na_2SO_4$, and evaporated. The product was purified via silica flash chromatography (40% EtOAc in hexanes).

Yield: 0.089 g, 58%.

$^1$H-NMR (400 MHz, CDCl$_3$): δ 1.15 (t, 3H), 1.28 (d, 3H), 1.70 (m, 1H), 1.90 (m, 1H), 2.22 (q, 2H), 2.60 (m, 1H), 3.07 (q, 2H), 3.73 (s, 3H), 5.85 (d, 1H), 5.95 (s, 1H), 6.90 (m, 1H).

(E)-Methyl 6-(4-hydroxy-3-((2E,4E)-2-methyldeca-2,4-dienoyl)-2-oxo-2H-pyran-6-yl)hept-2-enoate (IX in Scheme 2)

To (E)-Methyl 6-(4-hydroxy-2-oxo-3-propionyl-2-H-pyran-6-yl)hept-2-enoate (VII; 2 g; 6.5 mmol) in 80 ml anhydrous CH$_2$Cl$_2$ at −72° C., was added TiCl$_4$ (2.9 ml; 26.4 mmol; Aldrich) under argon. The reaction was stirred for 20 min, after which DIPEA (5.6 ml; 32.2 mmol; Aldrich) was added. After stirring at −72° C. for 3 h, trans 2-octenal (2.4 g; 20 mmol; Aldrich) in 20 ml anhydrous CH$_2$Cl$_2$ was added in two portions over 10 min. The reaction was stirred at −72° C. for 2 days, stirred at 0° C. for 1 h, quenched with 40 ml ice water, and extracted with 2×40 ml CH$_2$Cl$_2$. The pooled organic extracts was washed with saturated NH$_4$Cl, washed twice with saturated NaHCO$_3$, dried with anhydrous Na$_2$SO$_4$, and evaporated to a brown semi-solid. Compounds VIII (153 mg) and IX (161 mg) were isolated using cycles of silica flash chromatography (EtOAc gradient in hexanes).

VIII: Yield: 153 mg, 5.4%. $^1$H-NMR (400 MHz, CDCl$_3$): δ 0.88 (t, 3H), 1.15 (d, 3H), 1.30 (d, 3H) 1.20-1.40 (overlapping m, 6H), 1.66 (m, 1H) 1.88 (m, 1H), 2.01 (m, 2H), 2.20 (m, 2H) 2.55 (overlapping m, 2H), 3.72 (s; 3H), 4.49 (br s, 1H), 5.48 (dd, 1H), 5.72 (m, 1H), 5.85 (d, 1H), 5.95 (s, 1H), 6.90 (m, 1H).

IX: Yield: 161 mg, 5.9%. $^1$H-NMR (400 MHz, CDCl$_3$): δ 0.88 (t, 3H), 1.30 (d, 3H) 1.20-1.40 (overlapping m, 6H) 1.66 (m, 1H) 1.88 (m, 1H), 2.00 (s, 3H), 2.01 (m, 2H), 2.20 (m, 2H), 2.55 (m, 1H), 3.72 (s; 3H), 5.85 (d, 1H), 5.95 (s, 1H), 6.04 (m, 1H), 6.38 (t, 1H), 6.63 (d, 1H), 6.90 (m, 1H).

VIII was transformed to 1× using the following procedure: VIII (153 g; 0.352 mmol) was dissolved in 5 ml anhydrous benzene in a 20 ml screw-cap vial. p-Toluenesulfonic acid (63 mg; 0.702 mmol; Aldrich) was added, and the reaction was stirred at 80° C. for 2 h. Upon cooling, the reaction was quenched with 10 ml ice water and extracted with 2×10 ml EtOAc. The organic extracts were pooled, washed with saturated NaHCO$_3$, dried with brine and anhydrous Na$_2$SO$_4$, evaporated, and the product was purified via silica chromatography to give IX.

Yield: 68 mg, 45%.

(E)-6-(4-Hydroxy-3-((2E,4E)-2-methyldeca-2,4-dienoyl)-2-oxo-2H-pyran-6-yl)hept-2-enoic acid (X in Scheme 2)

To a solution of IX (100 mg; 0.24 mmol) in 20 ml THF, was added 5.2 ml 1 M LiOH (5.2 mmol; Aldrich). The reaction mixture was stirred for 35 h at 25° C. 15 ml EtOAc was added, and the reaction mixture was acidified with 3 N HCl to pH 2 and extracted with 3×10 ml EtOAc. The organic extracts were pooled, evaporated, and purified via semi-preparative RPC18-HPLC (Phenomenx Jupiter C18, 300 A°, 10 micron, 25 cm×10 mm column; mobile phase A, MeOH/H$_2$O/AcOH, 70/30/4, v/v/v; mobile phase B, MeOH/H$_2$O/AcOH, 90/10/4, v/v/v; gradient, 30 min 0% B, 50 min, 100% B; flow rate, 2 ml/min).

Yield: 23.4 mg, 24%.

$^1$H-NMR (400 MHz, CDCl$_3$): δ 0.88 (t, 3H), 1.30 (d, 3H) 1.20-1.40 (overlapping m, 6H), 1.66 (m, 1H) 1.88 (m, 1H), 2.00 (s, 3H), 2.01 (m, 2H), 2.20 (m, 2H), 2.60 (m, 1H), 5.85 (d, 1H), 5.95 (s, 1H), 6.04 (m, 1H), 6.38 (t, 1H), 6.63 (d, 1H), 7.00 (m, 1H).

Methyl ((E)-5-(4-hydroxy-3-((2E,4E)-2-methyldeca-2,4-dienoyl)-2-oxo-2H-pyran-6-yl)hex-1-en-1-yl) carbamate (XI in Scheme 2)

X (23 mg; 0.057 mmol) was dissolved in 4 ml acetone (distilled over P$_2$O$_5$) and cooled to 0° C. DIPEA (47.6 μl; 0.275 mmol; Aldrich) was added, followed by ethyl chloroformate (23.8 μl; 0.250 mmol; Aldrich). The reaction mixture was stirred for 90 min, after which NaN$_3$ (36 mg in 500 μl water, 0.57 mmol; Aldrich) was added and stirred for 70 min. 15 ml ice water was added, the reaction mixture was extracted with 3×20 ml toluene, and the pooled organic extracts were dried with anhydrous Na$_2$SO$_4$, and evaporated to an oil. The oil was left under high vacuum for 15 min, and then was dissolved in 4 ml anhydrous toluene, refluxed under argon for 2 h, cooled to 80° C., supplemented with 1.5 ml anhydrous MeOH, and maintained at 80° C. for 14 h. The sample was evaporated, and the product was purified via silica flash chromatography (EtOAc gradient in hexanes).

Yield: 15 mg, 60%.

$^1$H-NMR (400 MHz, CDCl$_3$): δ 0.88 (t, 3H), 1.25 (d, 3H) 1.30 (overlapping m, 6H), 1.60 (m, 1H) 1.80 (m, 1H), 2.01 (s, 3H), 2.05 (m, 2H), 2.18 (m, 2H), 2.60 (m, 1H), 4.95 (br s, 1H), 5.95 (s, 1H), 6.04 (m, 1H), 6.20 (br m, 1H), 6.35 (t, 1H), 6.45 (t, 1H), 6.62 (d, 1H).

MS (MALDI): calculated: m/z 432.23 (MH$^+$). Found: 432.23, 445.23.

Example 2

Methyl ((E)-5-(4-hydroxy-3-((2E,4E)-2-methylundeca-2,4-dienoyl)-2-oxo-2H-pyran-6-yl)hex-1-en-1-yl)carbamate (compound 2)

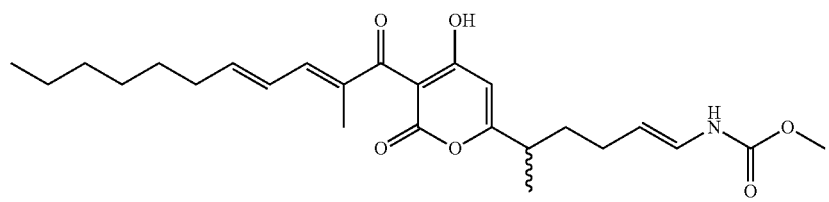

2

The compound was synthesized according to the methods described for Example 1. Trans 2-nonenal (Aldrich) was used instead of trans 2-octenal.

Yield (starting from VII): 10 mg, 0.34%.

$^1$H-NMR (400 MHz, CDCl$_3$): δ 0.88 (t, 3H), 1.25 (d, 3H) 1.30-1.40 (overlapping m, 8H), 1.60 (m, 1H) 1.80 (m, 1H), 2.01 (s, 3H), 2.05 (m, 2H), 2.18 (m, 2H), 2.60 (m, 1H), 4.95 (br s, 1H), 5.95 (s, 1H), 6.04 (m, 1H), 6.20 (br m, 1H), 6.35 (t, 1H), 6.45 (t, 1H), 6.62 (d, 1H).

MS (MALDI): calculated: m/z 446.25 (MH+). Found: 446.23, 468.23.

Example 3

Methyl ((E)-5-(4-hydroxy-3-((2E,4E)-2-methyl-dodeca-2,4-dienoyl)-2-oxo-2H-pyran-6-yl)hex-1-en-1-yl)carbamate (compound 3)

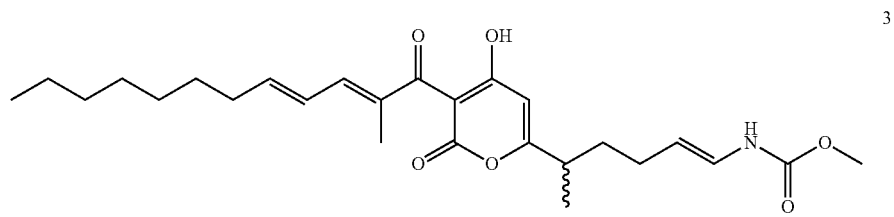 [SMILES: CCCCCCC/C=C/C=C(\C)C(=O)c1c(O)cc(C(C)CC/C=C/NC(=O)OC)oc1=O]

3

The compound was synthesized according to the methods described for Example 1. Trans 2-decenal (Aldrich) was used instead of trans 2-octenal.

Yield (starting from VII): 0.5 mg, 0.02%.

$^1$H-NMR (400 MHz, CDCl$_3$): δ 0.88 (t, 3H), 1.25 (d, 3H) 1.30-1.40 (overlapping m, 10H), 1.60 (m, 1H) 1.80 (m, 1H), 2.01 (s, 3H), 2.05 (m, 2H), 2.18 (m, 2H), 2.60 (m, 1H), 4.95 (br s, 1H), 5.95 (s, 1H), 6.04 (m, 1H), 6.20 (br m, 1H), 6.35 (t, 1H), 6.45 (t, 1H), 6.62 (d, 1H).

MS (MALDI): calculated: m/z 460.23 (MH+). Found: 460.23, 482.23.

Example 4 methyl ((E)-5-(4-hydroxy-3-((2E,4E)-2-methyl-trideca-2,4-dienoyl)-2-oxo-2H-pyran-6-yl)hex-1-enyl)carbamate (compound 4)

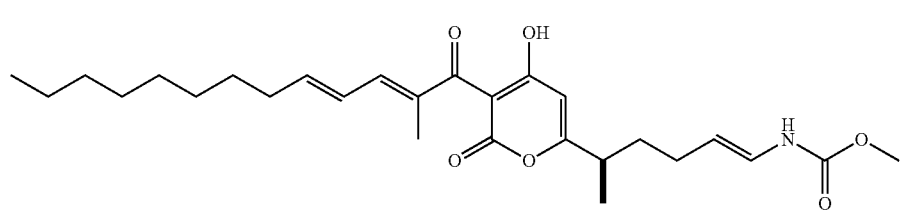

4

The compound was synthesized according to the methods described for Example 1. Trans 2-undecenal (Aldrich) was used instead of trans 2-octenal.

Yield (starting from VII): 2 mg, 0.07%.

$^1$H-NMR (400 MHz, CDCl$_3$): δ 0.88 (t, 3H), 1.25 (d, 3H) 1.30-1.42 (overlapping m, 10H), 1.42 (m, 2H), 1.60 (m, 1H) 1.80 (m, 1H), 2.01 (s, 3H), 2.05 (m, 2H), 2.18 (m, 2H), 2.60 (m, 1H), 4.95 (br s, 1H), 5.95 (s, 1H), 6.04 (m, 1H), 6.20 (br m, 1H), 6.35 (t, 1H), 6.45 (t, 1H), 6.62 (d, 1H).

MS (MALDI): calculated: m/z 474.28 (MH+). Found: 474.28, 496.28.

Example 5

Methyl ((E)-5-(3-(((2E,4E)-2,5-dimethyldeca-2,4-dienoyl)-4-hydroxy-2-oxo-2H-pyran-6-yl)pent-1-en-1-yl)carbamate (compound 5; XXVa in Scheme 3)

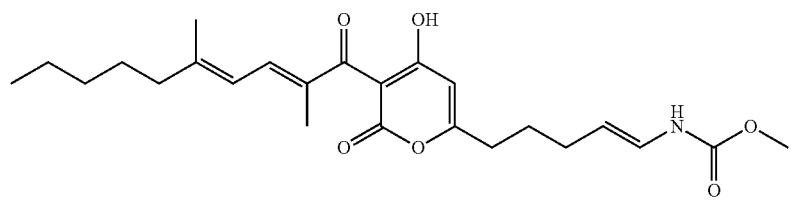

4-Hydroxy-6-methyl-3-propionyl-2H-pyran-2-one (XII in Scheme 3)

To 4-hydroxy-6-methyl-2H-pyran-2-one (18 g; 143 mmol; Aldrich) in 300 ml DCM at 0° C., was added TEA (20 ml; 143 mmol; Aldrich), DCC (30 g; 145 mmol; Aldrich), DMAP (5.25 g; 42.7 mmol; Aldrich) and propionic acid (11 ml; 147 mmol; Aldrich). The reaction mixture was stirred at 0° C. for 1 h, stirred at 25° C. for 18 h, and filtered via vacuum filtration. The filtrate was washed with 5% HCl, dried with brine and anhydrous $Na_2SO_4$, and evaporated to a white solid.

Yield: 15.7 g, 60%.

$^1$H-NMR (400 MHz, $CDCl_3$): δ 1.6 (t, 3H), 2.27 (s, 3H), 3.11 (t, 2H), 5.94 (s, 1H).

6-(4-((t-Butyldimethylsilyl)oxy)butyl)-4-hydroxy-3-propionyl-2H-pyran-2-one (XIV in Scheme 3)

To 4-hydroxy-6-methyl-3-propionyl-2H-pyran-2-one (XII; 7 g, 38.5 mmol) in 60 ml anhydrous THF at −72° C. under argon, was added freshly prepared LDA (18.5 ml DIPEA in 150 ml THF with 52 ml 2.5 M n-butyllithium, Aldrich) in 150 ml anhydrous THF, and 20 ml HMPA (Aldrich). The reaction mixture was stirred for 1 h. 3-bromopropoxy-t-butyldimethylsilane (7 ml g; 27.7 mmol; Aldrich) in 50 ml anhydrous THF was added over 30 min, and stirred for an additional 5 min. The reaction mixture was quenched with saturated $NH_4Cl$, extracted with 3×150 ml EtOAc, dried with brine and anhydrous $Na_2SO_4$, and evaporated to a yellowish oil. The product was purified via silica flash chromatography.

Yield: 5 g, 37%.

$^1$H-NMR (400 MHz, $CDCl_3$): δ 0.06 (s, 6H), 0.90 (s, 9H), 1.20 (t, 3H), 1.57 (t, 2H), 1.72 (t, 2H), 2.56 (t, 2H), 3.10 (t, 2H), 3.63 (t, 2H), 5.95 (s; 1H).

4-hydroxy-6-(4-hydroxybutyl)-3-propionyl-2H-pyran-2-one (XV in Scheme 3)

6-(4-((t-Butyldimethylsilyl)oxy)butyl)-4-hydroxy-3-propionyl-2H-pyran-2-one (XIV; 5 g; 14.1 mmol) in 150 ml AcOH/THF/water (3/1/1, v/v/v) was stirred at 28° C. for 18 h. The reaction mixture was neutralized with saturated $NaHCO_3$, extracted with 3×150 ml EtOAc, dried with $Na_2SO_4$, and evaporated to an oil. The product was purified via silica chromatography (40% EtOAc in hexanes).

Yield: 2.62 g, 77%.

$^1$H-NMR (400 MHz, $CDCl_3$): δ 1.20 (t, 3H), 1.57 (t, 2H), 1.72 (t, 2H), 2.56 (t, 2H), 3.10 (q, 2H), 3.70 (t, 2H), 5.95 (s; 1H).

4-(4-Hydroxy-2-oxo-3-propionyl-2H-pyran-6-yl) butanal (XVI in Scheme 3)

To 4-hydroxy-6-(4-hydroxybutyl)-3-propionyl-2H-pyran-2-one (XV; 1.47 g; 6.12 mmol) in 60 ml $CH_2Cl_2$ and 2.19 ml pyridine, was added sodium periodinate (6.13 g; 15.3 mmol; Aldrich). The reaction was stirred at 28° C. for 3 h, neutralized with saturated $NaHCO_3$, extracted with 3×150 ml $CH_2Cl_2$, dried with brine and $Na_2SO_4$, and evaporated. The product was purified via silica flash chromatography (20% EtOAc in hexanes).

Yield: 1.01 g, 70%.

$^1$H-NMR (400 MHz, $CDCl_3$): δ 1.20 (t, 3H), 2.00 (m, 2H), 2.58 (m, 4H), 3.10 (q, 2H), 5.95 (s; 1H), 9.80 (s, 1H).

(E)-Methyl 6-(4-hydroxy-2-oxo-3-propionyl-2H-pyran-6-yl)hex-2-enoate (XVII in Scheme 3)

NaH (0.4 g; 10 mmol; 60% dispersion in mineral oil; Aldrich) was added to trimethyl phosphonoacetate (1.90 g; 10 mmol; Aldrich) in 25 ml THF. The reaction was stirred at 25° C. for 15 min, after which 4-(4-hydroxy-2-oxo-3-propionyl-2H-pyran-6-yl)butanal (XVI; 1.01 g; 4.3 mmol) in 40 ml THF was added. The reaction mixture was stirred at 25° C. for 2 h, quenched with saturated $NH_4Cl$, extracted with 3×30 ml EtOAc, dried with anhydrous $Na_2SO_4$, and evaporated. The product was purified via silica flash chromatography (EtOAc gradient in hexanes).

Yield: 0.78 g, 63%.

$^1$H-NMR (400 MHz, $CDCl_3$): δ 1.20 (t, 3H), 1.85 (m, 2H), 2.25 (t, 2H), 2.50 (t, 2H), 3.10 (q, 2H), 3.75 (s, 3H), 5.90 (d, 1H), 5.95 (s; 1H), 6.80 (m, 1H).

(E)-Ethyl 3-methyl 2-octenoate (XIX in Scheme 3)

To a suspension of CuI (10.34 g; 54.3 mmol; Aldrich) in 150 ml anhydrous THF in an acetonitrile/dry-ice bath at −40° C., was added 2.2M n-pentyllithium in heptane (48.2 ml; 106 mmol; Aldrich). After stirring for 30 min, the acetonitrile/dry-ice bath at −40° C. was replaced by an ethanol/dry-ice bath at −72° C. Ethyl 2-butynoate (XVIII; 10.05 g; 89.6 mmol; Aldrich) in 10 ml THF was added in three portions over 10 min, the suspension was stirred for an additional 30 min, and the reaction was quenched by addition of 10 ml methanol, followed by 50 ml saturated $NH_4Cl$, with stirring. The ethanol/dry-ice bath was removed, and the suspension was allowed to reach room temperature. The suspension was filtered, and the solid was rinsed with ether. The filtrate was extracted 3× with ether, and the organic extracts were pooled, dried with anhydrous sodium sulfate, and evaporated to 16 g of yellowish oil.

Yield: 16 g, 97% crude.

(E)-3-methyl-2-octenol (XX in Scheme 3)

(E)-Ethyl 3-methyl 2-octenoate (XIX; 16 g; 87 mmol) was dissolved in 160 ml anhydrous THF and brought to −72° C. 1

M DIBAH in hexanes (190 ml; 190 mmol; Aldrich) was added slowly under argon, 2.01 (m, 2H), and the reaction mixture was stirred for an additional 30 min. The dry-ice bath was removed, and the reaction mixture was stirred for an additional 1 h at room temperature. 200 ml ether was added, and the reaction mixture was cooled to 0° C. 8.2 ml water, 8.2 ml 15% NaOH, 20 ml water successively were added, and the ice bath was removed, and the reaction mixture was stirred for 15 min at 25° C. The reaction mixture was dried with anhydrous $MgSO_4$ and stirred for an additional 15 min. The reaction mixture was filtered, and the filtrate was evaporated to 9 g of yellow oil. The desired alcohol distilled at 85-90° C. under 10 torn Yield: 6 g, 60%.

$^1$H-NMR (400 MHz, $CDCl_3$): δ 0.90 (t, 3H), 1.25 (m, 2H), 1.32 (m, 2H), 1.40 (m, 2H), 1.66 (s, 3H), 2.01 (t, 2H), 4.15 (t, about 20% Z isomer, 2H), 5.41 (t, 2H).

(E) 3-Methyl-2-octenal (XXI in Scheme 3)

(E)-3-Methyl-2-octenol (XX; 3 g; 21.4 mmol) was dissolved in 45 ml $CH_2Cl_2$. To the solution, was added 10 g 4A° molecular sieves (Aldrich), NMO (4.9 g; 41.8 mmol; Aldrich) and TPAP (0.44 g; 1.25 mmol; Aldrich). The suspension was stirred in the dark under argon for 30 min. The product was purified via silica chromatography (eluent: $CH_2Cl_2$). XXI was unstable and was used the same day or stored under argon at −78° C.

Yield: 2.6 g, 87%.

$^1$H-NMR (400 MHz, $CDCl_3$): δ 0.90 (t, 3H), 1.25 (m, 2H), 1.32 (m, 2H), 1.40 (m, 2H), 1.6 (s, 3H), 2.01 (t, 2H), 5.89 (d; 1H), 9.99 (d, 1H).

(2E)-Methyl 6-(3-((2E)-2,5-dimethyldeca-2,4-dienoyl)-4-hydroxy-2-oxo-2,1-pyran-6-yl)hex-2-enoate (XXIII in Scheme 3)

To ((E)-methyl 6-(4-hydroxy-2-oxo-3-propionyl-2H-pyran-6-yl)hex-2-enoate (XVII; 0.78 g; 2.6 mmol) in 30 ml anhydrous $CH_2Cl_2$ at −72° C., was added $TiCl_4$ (1.2 ml; 10.4 mmol; Aldrich) under argon, and the reaction mixture was stirred for 60 min. DIPEA (2.2 ml; 13 mmol; Aldrich) was added, the reaction mixture was stirred for 90 min, and (E)-3-methyl-2-octenal (XXI; 1.10 g; 7.8 mmol) in 20 ml anhydrous $CH_2Cl_2$ was added in 2 portions over 10 min. The reaction was stirred at −72° C. for 48 h, stirred at 0° C. for 1 h, quenched with 40 ml ice water, and extracted with 2×50 ml $CH_2Cl_2$. The pooled organic extracts was washed with saturated $NH_4Cl$, washed twice with saturated $NaHCO_3$, dried with anhydrous $Na_2SO_4$, and evaporated to a brown semisolid. XXII (205 mg) and XXIII (35 mg) were isolated by cycles of silica flash chromatography using (EtOAc gradient in hexanes).

XXII: Yield: 205 mg, 18%.

$^1$H-NMR (400 MHz, $CDCl_3$): δ 0.90 (t, 3H), 1.12 (d, 3H), 1.25 (br m, 4H), 1.45 (m, 2H), 1.74 (s, 3H), 1.83 (q, 2H), 2.10 (t, 2H), 2.24 (m, 2H) 2.50 (t, 2H), 2.59 (m, 1H), 3.75 (s; 3H), 5.00 (t, 1H), 5.35 (d, 1H), 5.85 (d, 1H), 5.95 (s, 1H), 6.95 (m, 1H).

XXIII: Yield: 35 mg, 3.23%.

$^1$H-NMR (400 MHz, $CDCl_3$): δ 0.90 (t, 3H), 1.25 (br m, 4H), 1.45 (m, 2H), 1.85 (s, 3H), 2.01 (s, 3H), 2.08 (m, 2H), 2.22 (m, 2H), 250 (t, 2H), 2.58 (t, 2H), 3.75 (s; 3H), 5.85 (d, 1H), 5.95 (s, 1H), 6.95 (m, 2H).

XXII was transformed to XIII using the same procedure as for VIII and IX: XXII (205 mg; 0.472 mmol) was dissolved in 5 ml anhydrous benzene in a 20 ml screw-cap vial. p-Toluenesulfonic acid (190 mg; 1 mmol; Aldrich) was added, and the reaction mixture was stirred at 80° C. for 2 h. Upon cooling, the reaction was quenched with 10 ml ice water and extracted with 2×10 ml EtOAc. The organic extracts were pooled, washed with saturated $NaHCO_3$, dried with brine and anhydrous $Na_2SO_4$, and the product was isolated via silica chromatography.

Yield: 91 mg, 50%.

(2E)-6-(3-((2E)-2,5-dimethyldeca-2,4-dienoyl)-4-hydroxy-2-oxo-2H-pyran-6-yl)hex-2-enoic acid (XXIV in Scheme 3)

To XXIII (91 mg, 211 μmol) in 20 ml THF, was added 5.2 ml 1 M LiOH (52 mmol; Aldrich), and the reaction mixture was stirred at 25° C. for 35 h. 15 ml EtOAc and 5 ml saturated $NH_4Cl$ were added, and the reaction mixture was acidified with 3N HCl to pH 2 and extracted with 2×15 ml EtOAc. The organic extracts were pooled, evaporated, and purified via semi-preparative RPC18-HPLC (Phenomenx Jupiter C18, 300 A°, 10 micron, 25 cm×10 mm column; mobile phase A, $MeOH/H_2O/AcOH$, 70/30/4, v/v/v; mobile phase B, $MeOH/H_2O/AcOH$, 90/10/4, v/v/v; gradient, 30 min 0% B, 50 min, 100% B; flow rate, 2 ml/min). XXIVa eluted at 38 min. XXIVb eluted at 23 min.

XXIVa: Yield: 22 mg, 25%.

$^1$H-NMR (400 MHz, $CDCl_3$): δ 0.90 (t, 3H), 1.20-1.40 (m, 4H), 1.50 (m, 1H), 1.70 (m, 1H), 1.84 (s, 3H), 2.00 (s, 3H), 2.16 (m, 2H), 2.26 (m, 2H), 2.50 (t, 2H), 2.60 (m, 2H), 5.82 (d; 1H), 5.91 (s, 1H), 6.18 (d, 1H), 6.98-7.08 (ovrlp d, 2H).

XXIVb: Yield: 15 mg, 17%.

$^1$H-NMR (400 MHz, $CDCl_3$): δ 0.90 (t, 3H), 1.20-1.40 (m, 4H), 1.50 (m, 1H), 1.70 (m, 1H), 1.94 (s, 3H), 2.00 (s, 3H), 2.16 (m, 2H), 2.26 (m, 2H), 2.50 (t, 2H), 2.60 (m, 2H), 5.82 (d; 1H), 5.91 (s, 1H), 6.18 (d, 1H), 6.98-7.08 (ovrlp d, 2H).

Methyl ((E)-5-(3-((2E,4E)-2,5-dimethyldeca-2,4-dienoyl)-4-hydroxy-2-oxo-2H-pyran-6-yl)pent-1-en-1-yl)carbamate (XXVa in Scheme 3)

XXIVa (18.5 mg; 46.2 μmol) was dissolved in 3 ml acetone (distilled over $P_2O_5$) and cooled to 0° C. DIPEA (37.2 μl; 222 mmol; Aldrich) was added, ethyl chloroformate (18.5 μl, 231 mmol; Aldrich), was added, and the reaction mixture was stirred for 90 min. $NaN_3$ (29 mg in 400 μl water, 462 μmmol; Aldrich) was added, and the reaction mixture was stirred for 70 min. 15 ml ice water was added, the reaction mixture was extracted with 3×20 ml toluene, and the pooled organic extracts were dried with anhydrous $Na_2SO_4$, and evaporated to an oil. The oil was left under high vacuum for 15 min, and then was dissolved in 3 ml anhydrous toluene, refluxed under argon for 2 h, cooled to 80° C., supplemented with 1.5 ml anhydrous MeOH, and maintained at 80° C. for 14 h. The sample was evaporated, and the product was purified via silica flash chromatography (EtOAc gradient in hexanes).

Yield: 6.1 mg, 57%.

$^1$H-NMR (400 MHz, $CDCl_3$): δ 0.90 (t, 3H), 1.20-1.40 (br m, 6H), 1.50 (m, 2H), 1.75 (m, 2H), 1.84 (s, 3H), 2.00 (s, 3H), 2.18 (t, 2H), 2.49 (t, 2H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 432.23 (MH$^+$). Found: 432.23, 445.23.

Example 6

Methyl ((E)-5-(3-((2E,4Z)-2,5-dimethyldeca-2,4-dienoyl)-4-hydroxy-2-oxo-2H-pyran-6-yl)pent-1-en-1-yl)carbamate (compound 10; XXVb in Scheme 3)

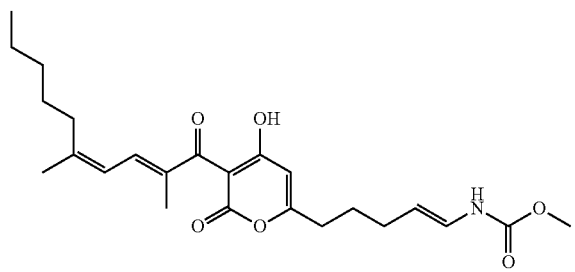

XXIVb (11.5 mg; 28.6 μmol; Example 5) was dissolved in 2 ml acetone (distilled over P$_2$O$_5$) and cooled to 0° C. DIPEA (23.1 μl; 137 μmol; Aldrich) was added, ethyl chloroformate (11.5 μl, 143 μmmol, Aldrich) was added, and the reaction was stirred for 90 min. NaN$_3$ (18 mg in 300 μl water, 286 μmol; Aldrich) was added, and the reaction mixture was stirred for 70 min. 15 ml ice water was added, and the reaction mixture was extracted with 3×20 ml toluene, and the pooled organic extracts were dried with anhydrous Na$_2$SO$_4$, and evaporated to an oil. The oil was left under high vacuum for 15 min, and then was dissolved in 2 ml anhydrous toluene, refluxed under argon for 2 h, cooled to 80° C., supplemented with 1 ml anhydrous MeOH, and maintained at 80° C. for 14 h. The sample was evaporated, and the product was purified via silica flash chromatography (EtOAc gradient in hexanes).

Yield: 5 mg, 42%.

$^1$H-NMR (400 MHz, CDCl$_3$): δ 0.90 (t, 3H), 1.20-1.40 (br m, 6H), 1.50 (m, 2H), 1.75 (m, 2H), 1.94 (s, 3H), 2.00 (s, 3H), 2.18 (t, 2H), 2.49 (t, 2H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 432.23 (MO. Found: 432.23, 445.23.

Example 7

Methyl ((E)-5-(3-((2E,4E)-2,5-dimethylundeca-2,4-dienoyl)-4-hydroxy-2-oxo-2H-pyran-6-yl)pent-1-en-1-yl)carbamate (compound 6)

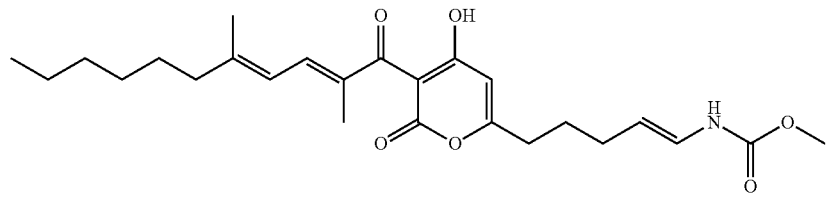

The compound was synthesized according to the methods described for Example 5, using n-hexyllithium (Aldrich) in place of n-pentyllithium, and using (E)-3-methyl-2-nonenal in place of (E)-3-methyl-2-octenal.

Yield (starting from XVII): 20 mg, 1.7%.

$^1$H-NMR (400 MHz, CDCl$_3$): δ 0.90 (t, 3H), 1.20-1.40 (br m, 8H), 1.50 (m, 2H), 1.75 (m, 2H), 1.84 (s, 3H), 2.00 (s, 3H), 2.18 (t, 2H), 2.49 (t, 2H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 446.25 (MH$^+$). Found: 446.25, 468.25.

Example 8

Ethyl ((E)-5-(3-((2E,4E)-2,5-dimethylundeca-2,4-dienoyl)-4-hydroxy-2-oxo-2H-pyran-6-yl)pent-1-en-1-yl)carbamate (compound 7)

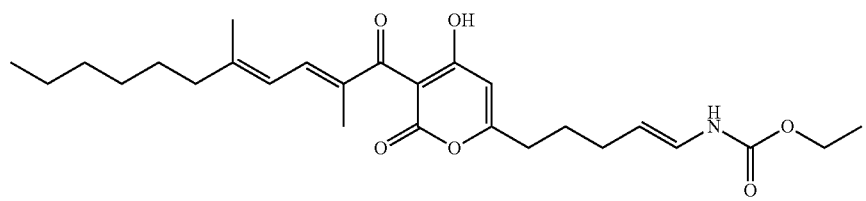

The compound was synthesized according to the methods described for Example 7, using ethanol in place of MeOH in the final step.

Yield (starting from XVII): 10 mg, 0.88%

$^1$H-NMR (400 MHz, CDCl$_3$): δ 0.90 (t, 3H), 1.20-1.40 (br m, 9H), 1.45 (m, 2H), 1.65 (m, 2H), 1.84 (s, 3H), 2.00 (s, 3H), 2.10 (m, 2H), 2.16 (m, 2H), 2.49 (t, 2H), 4.18 (q, 2H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 460.22 (MH$^+$). Found: 460.22, 482.27.

Example 9

Methyl ((E)-5-(3-((2E,4E)-2,5-dimethylnona-2,4-dienoyl)-4-hydroxy-2-oxo-2H-pyran-6-yl)pent-1-en-1-yl)carbamate (7-desmethyl-Myx B)

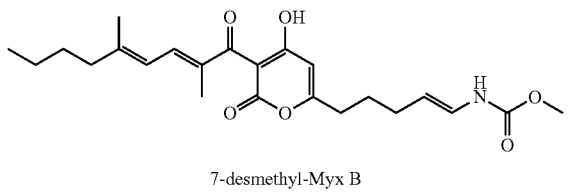 [SMILES: CCCC/C(C)=C/C=C(\C)C(=O)c1c(O)cc(CCC/C=C/NC(=O)OC)oc1=O]

7-desmethyl-Myx B

The compound was synthesized according to the methods described for Example 5, using n-butyllithium (Aldrich) in place of n-pentyllithium, and using (E)-3-methyl-2-heptenal in place of (E)-3-methyl-2-octenal.

Yield (starting from XVII): 20 mg, 1.8%.

$^1$H-NMR (400 MHz, CDCl$_3$): δ 0.90 (t, 3H), 1.20-1.40 (br m, 4H), 1.65 (m, 2H), 1.75 (m, 2H), 1.84 (s, 3H), 2.00 (s, 3H), 2.18 (t, 2H), 2.49 (t, 2H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 418.22 (MH$^+$). Found: 418.52, 430.52.

Example 10

Methyl ((E)-5-(3-((2E,4Z)-2,5-dimethylnona-2,4-dienoyl)-4-hydroxy-2-oxo-2H-pyran-6-yl)pent-1-en-1-yl)carbamate (7-desmethyl-Myx B, E/Z isomer)

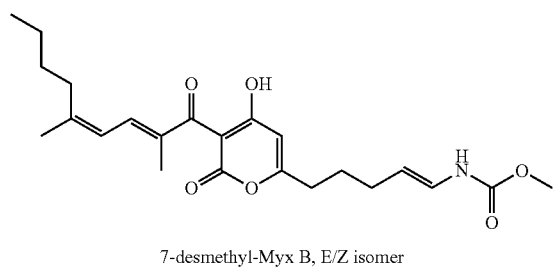 [SMILES: CCCC/C(C)=C\C=C(/C)C(=O)c1c(O)cc(CCC/C=C/NC(=O)OC)oc1=O]

7-desmethyl-Myx B, E/Z isomer

The compound was synthesized according to the methods described for Example 5 and Example 6, using (E)-3-methyl-2-heptenal (Example 9) in place of (E)-3-methyl-2-octenal.

Yield (starting from XVII): 15 mg, 1.3%.

$^1$H-NMR (400 MHz, CDCl$_3$): δ 0.90 (t, 3H), 1.20-1.40 (br m, 4H), 1.65 (m, 2H), 1.75 (m, 2H), 1.93 (s, 3H), 2.00 (s, 3H), 2.18 (t, 2H), 2.49 (t, 2H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 418.22 (MH$^+$). Found: 418.52, 430.52.

Example 11

Methyl ((E)-5-(3-((2E,4E)-2,5-dimethyldeca-2,4-dienoyl)-4-hydroxy-2-oxo-2H-pyran-6-yl)hex-1-en-1-yl)carbamate (compound 8; XXIXa in Scheme 4)

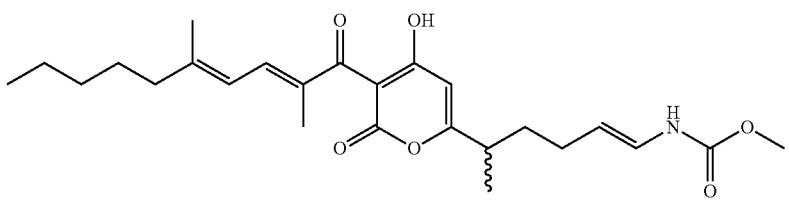

(2E)-Methyl 6-(3-((2E)-2,5-dimethyldeca-2,4-dienoyl)-4-hydroxy-2-oxo-2H-pyran-6-yl)hept-2-enoate (XXVII in Scheme 4)

To (E)-methyl 6-(4-hydroxy-2-oxo-3-propionyl-2-H-pyran-6-yl)hept-2-enoate (VII; 0.63 g, 2.05 mmol) in 30 ml anhydrous CH$_2$Cl$_2$ at −72° C., was added titanium tetrachloride (0.88 ml; 8 mmol; Aldrich) under argon, and the reaction mixture was stirred for 20 min. DIPEA (1.64 ml; 9.43 mmol; Aldrich) was added, and the reaction mixture was stirred for 90 min. (E)-3-methyl-octenal (XXI; 1 g; 7.25 mmol) in 5 ml anhydrous CH$_2$Cl$_2$ was added in two portions over 10 min, and the reaction mixture was stirred at −72° C. for 48 h and at 0° C. for 1 hour. The reaction was quenched with 40 ml ice water and extracted with 2×40 ml CH$_2$Cl$_2$. The CH$_2$Cl$_2$ extracts were pooled, washed with saturated NH$_4$Cl, washed twice with saturated NaHCO$_3$, and dried with anhydrous Na$_2$SO$_4$. The product was purified by silica flash chromatography (EtOAc gradient in hexanes).

Yield: 94 mg; 10.75%

$^1$H-NMR (400 MHz, CDCl$_3$): 0.90 (t, 3H), 1.20-1.40 (ovrlp d and m, 9H), 1.70 (m, 1H), 1.84 (s, 3H), 1.90 (s, unclear), 2.00 (s, 3H), 2.15 (m, 2H), 2.20 (m, 2H), 2.60 (m, 1H), 3.70 (s, 3H), 5.82 (d; 1H), 5.91 (s, 1H), 6.18 (d, 1H), 6.90 (m, 1H), 7.00 (d, 1H).

(E)-6-(3-((2E,4E)-2,5-dimethyldeca-dienoyl)-4-hydroxy-2-oxo-2H-pyran-6-yl)hept-2-oic acid (XXVIII in Scheme 4)

To XXVII (94 mg; 219 μmmol) in 12 ml THF, was added 3.2 ml 1M LiOH (3200 μmmol; Aldrich), and the reaction mixture was stirred for 35 h. 15 ml EtOAc and 5 ml saturated NH4Cl were added, and the reaction mixture was acidified with 1N HCl to pH 3 and extracted with 2×15 ml EtOAc. The organic extracts were pooled, dried with $Na_2SO_4$ and purified via semi-preparative RPC18-HPLC (Phenomenx Jupiter C18, 300 A°, 10 micron, 25 cm×10 mm column; mobile phase A, MeOH/$H_2O$/AcOH, 70/30/4, v/v/v; mobile phase B, MeOH/$H_2O$/AcOH, 90/10/4, v/v/v; gradient, 30 min 0% B, 50 min, 100% B; flow rate, 2 ml/min). XXVIIIa eluted at 42 min. XXVIIIb eluted at 26 min.

XXVIIIa: Yield, 20 mg, 22%.

$^1$H-NMR (400 MHz, $CDCl_3$): δ 0.90 (t, 3H), 1.20-1.40 (ovrlp d and m, 9H), 1.50 (m, 1H), 1.70 (m, 1H), 1.84 (s, 3H), 2.00 (s, 3H), 2.16 (m, 2H), 2.26 (m, 2H), 2.60 (m, 1H), 5.82 (d; 1H), 5.91 (s, 1H), 6.18 (d, 1H), 6.98-7.08 (ovrlp d and m, 2H)

XXVIIIb: Yield, 15.4 mg, 17%.

$^1$H-NMR (400 MHz, $CDCl_3$): δ 0.90 (t, 3H), 1.20-1.40 (ovrlp d and m, 9H), 1.50 (m, 1H), 1.70 (m, 1H), 1.91 (s, 3H), 2.10 (s, 3H), 2.16 (m, 2H), 2.26 (m, 2H), 2.60 (m, 1H), 5.82 (d; 1H), 5.91 (s, 1H), 6.18 (d, 1H), 6.98-7.08 (ovrlp d and m, 2H).

Methyl ((E)-5-(3-((2E,4E)-2,5-dimethyldeca-2,4-dienoyl)-4-hydroxy-2-oxo-2H-pyran-6-yl)hex-1-en-1-yl)carbamate (XXIXa in Scheme 4)

XXVIIIa (10 mg; 24 μmmol) was dissolved in 3 ml acetone (distilled over $P_2O_5$) and cooled to 0° C. DIPEA (23.1 μl; 115 μmol) was added, ethyl chloroformate (11.5 μl; 120 μmol) was added, and the reaction mixture was stirred for 90 min, $NaN_3$ (16 mg; 240 μmol) in 300 μl water was added, and the reaction mixture was stirred for 70 min. 15 ml ice water was added, and the reaction mixture was extracted with 3×20 ml toluene. The organic extracts were pooled, dried with anhydrous $Na_2SO_4$, and evaporated to an oil. The oil was left under high vacuum for 15 min, and then was dissolved in 2 ml anhydrous toluene, refluxed under argon for 2 h, cooled to 80° C., supplemented with 1 ml anhydrous MeOH, and maintained at 80° C. for 14 h. The sample was evaporated, and the product was purified via silica flash chromatography (EtOAc gradient in hexanes).

Yield: 6.1 mg, 57%

$^1$H-NMR (400 MHz, $CDCl_3$): δ 0.90 (t, 3H), 1.20-1.40 (ovrlp d and m, 9H), 1.75 (m, 2H), 1.83 (s, 3H), 2.00 (s, 3H), 2.08 (m, 2H), 2.18 (t, 2H), 2.60 (t, 1H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 44.25 ($MH^+$). Found: 446.52, 467.52.

Example 12

Methyl ((E)-5-(3-((2E,4Z)-2,5-dimethyldeca-2,4-dienoyl)-4-hydroxy-2-oxo-2H-pyran-6-yl)hex-1-en-1-yl)carbamate (compound 11; XXIXb in Scheme 4)

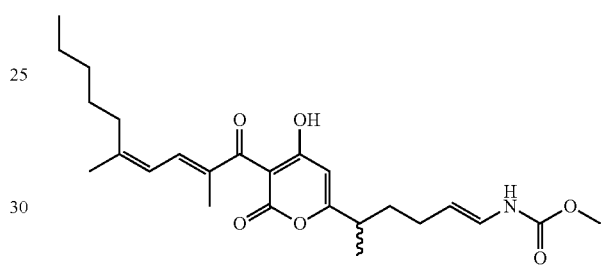

11

XXIXb was synthesized as in Example 6, using XXVIIIb (Example 11) in place of XXIVb.

Yield (starting from VII): 4 mg, 0.44%.

$^1$H-NMR (400 MHz, $CDCl_3$): δ 0.90 (t, 3H), 1.20-1.40 (ovrlp d and m, 9H), 1.75 (m, 2H), 1.93 (s, 3H), 2.00 (s, 3H), 2.08 (m, 2H), 2.18 (t, 2H), 2.60 (t, 1H), 3.72 (s, 3H), 4.94 (br m; 1H), 5.93 (s, 1H), 6.15 (d, 1H), 6.20 (br d, 1H), 6.46 (t, 1H), 6.98 (d, 1H).

MS (MALDI): calculated: m/z 44.25 ($MH^+$). Found: 446.52, 467.52.

Example 14

Methyl ((E)-5-(3-((2E,4E)-2,5-dimethylundeca-2,4-dienoyl)-4-hydroxy-2-oxo-2H-pyran-6-yl)hex-1-en-1-yl)carbamate (compound 9)

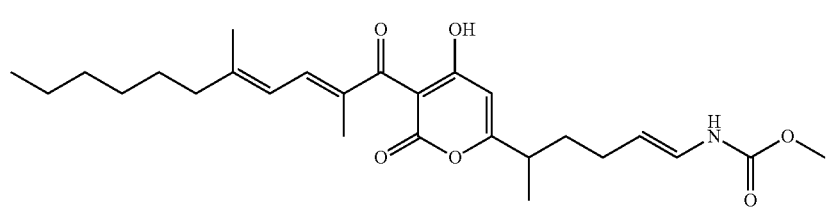

9

The compound was synthesized as in Example 11, using (E)-3-methyl-2-nonenal (Example 7) in place of (E)-3-methyl-2-octenal. Yield (starting from VII): 10 mg, 1.1%. $^1$H-NMR (400 MHz, CDCl$_3$): δ 0.90 (t, 3H), 1.20-1.40 (ovrlp d and m, 9H), 1.50 (m, 2H), 1.75 (m, 2H), 1.83 (s, 3H), 2.00 (s, 3H), 2.08 (m, 2H), 2.18 (t, 2H), 2.60 (t, 1H), 3.72 (s, 3H), 4.94 (br m; 1H), 5.93 (s, 1H), 6.15 (d, 1H), 6.20 (br d, 1H), 6.46 (t, 1H), 6.98 (d, 1H).MS (MALDI): calculated: m/z 460.27 (MH$^+$). Found: 460.52, 482.52.

Example 15

Methyl ((E)-5-(3-((2E,4E)-2,5-dimethylnona-2,4-dienoyl)-4-hydroxy-2-oxo-2H-pyran-6-yl)hex-1-en-1-yl)carbamate (Myx B)

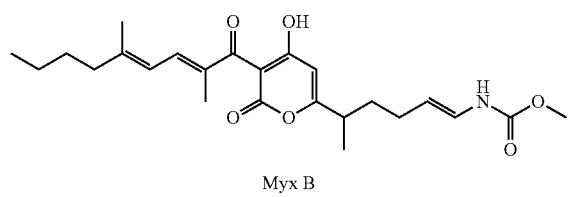 [SMILES: CCCC/C(C)=C/C=C(\C)C(=O)c1c(O)cc(C(C)CC/C=C/NC(=O)OC)oc1=O]

Myx B

The compound was synthesized as in Example 11, using (E)-3-methyl-2-heptenal (Example 9) in place of (E)-3-methyl-2-octenal. Yield (starting from VII): 20 mg, 2.3%. $^1$H-NMR (400 MHz, CDCl$_3$): δ 0.90 (t, 3H), 1.20 (d, 3H), 1.30 (m, 4H), 1.50 (m, 1H), 1.55 (m, 1H), 1.83 (s, 3H), 1.98 (s, 3H), 2.10 (m, 2H), 2.18 (t, 2H), 2.60 (t, 1H), 3.72 (s, 3H), 4.94 (br m; 1H), 5.93 (s, 1H), 6.15 (d, 1H), 6.20 (br d, 1H), 6.46 (t, 1H), 6.98 (d, 1H).
MS (MALDI): calculated: m/z 432.52 (MH$^+$). Found: 432.52, 445.52.

Example 16

Methyl ((E)-5-(3-((2E,4Z)-2,5-dimethylnona-2,4-dienoyl)-4-hydroxy-2-oxo-2H-pyran-6-yl)hex-1-en-1-yl)carbamate (Myx B, E/Z isomer)

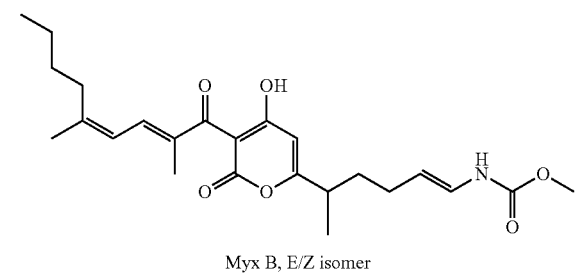 [SMILES: CCCC/C(C)=C\C=C(/C)C(=O)c1c(O)cc(C(C)CC/C=C/NC(=O)OC)oc1=O]

Myx B, E/Z isomer

The compound was synthesized as in Examples 11 and 12, using (E)-3-methyl-2-heptenal (Example 9) in place of (E)-3-methyl-2-octenal. Yield (starting from VII): 15 mg, 1.7%. $^1$H-NMR (400 MHz, CDCl$_3$): δ 0.90 (t, 3H), 1.20 (d, 3H), 1.30 (m, 4H), 1.50 (m, 1H), 1.55 (m, 1H), 1.94 (s, 3H), 1.98 (s, 3H), 2.10 (m, 2H), 2.18 (t, 2H), 2.60 (t, 1H), 3.72 (s, 3H), 4.94 (br m; 1H), 5.93 (s, 1H), 6.15 (d, 1H), 6.20 (br d, 1H), 6.46 (t, 1H), 6.98 (d, 1H).
MS (MALDI): calculated: m/z 432.52 (MH$^+$). Found: 432.52, 445.52.

Example 17

Assay of Inhibition of Bacterial RNA Polymerase

Example 17.1

Assay of Inhibition of *Escherichia coli* RNA Polymerase

Fluorescence-detected RNA polymerase assays with *E. coli* RNA polymerase were performed by a modification of the procedure of Kuhlman et al., 2004 [Kuhlman, P., Duff, H. & Galant, A. (2004) A fluorescence-based assay for multi-subunit DNA-dependent RNA polymerases. *Anal. Biochem.* 324, 183-190]. Reaction mixtures contained (20 μl): 0-100 nM test compound, 75 nM *E. coli* RNA polymerase σ$^{70}$ holoenzyme, 20 nM 384 bp DNA fragment containing the bacteriophage T4 N25 promoter, 100 μM ATP, 100 μM GTP, 100 μM UTP, 100 μM CTP, 50 mM Tris-HCl, pH 8.0, 100 mM KCl, 10 mM MgCl$_2$, 1 mM DTT, 10 μg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 μl 5 mM CaCl$_2$ and 2 U DNaseI (Ambion, Inc.), followed by incubation for 90 min at 37° C. RNA was quantified by addition of 100 μl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC50 is defined as the concentration of inhibitor resulting in 50% inhibition of RNA polymerase activity.

Example 17.2

Assay of Inhibition of *Mycobacterium tuberculosis* RNA Polymerase

Fluorescence-detected RNA polymerase assays with *M. tuberculosis* RNA polymerase were performed as in Example 17.1, using reaction mixtures containing (20 μl): 0-100 nM test compound, 75 nM *M. tuberculosis* RNA polymerase core enzyme, 300 nM *M. tuberculosis* σ$^A$, 20 nM 384 bp DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM MgCl$_2$, 2.5 mM DTT, and 12.7% glycerol. IC50 is defined as the concentration of inhibitor resulting in 50% inhibition of RNA polymerase activity.

Example 17.3

Assay of Inhibition of *Staphylococcus aureus* RNA Polymerase

Fluorescence-detected RNA polymerase assays with *S. aureus* RNA polymerase were performed as in Example 17.1, using reaction mixtures containing (20 μl): 0-100 nM test compound, 75 nM *S. aureus* RNA polymerase core enzyme, 300 nM *S. aureus* σ$^A$, 20 nM 384 bp DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM MgCl$_2$, 2.5 mM DTT, and 12.7% glycerol.

IC50 is defined as the concentration of inhibitor resulting in 50% inhibition of RNA polymerase activity.

Example 18

Assay of Inhibition of Bacterial Growth in Culture

Minimum inhibitory concentrations (MICs) for *Staphylococcus aureus* ATCC 12600, *Enterococcus faecalis* ATCC 19433, *Acinetobacter* baumannii ATCC 19606, and *Escherichia coli* D21f2tolC were quantified using spiral gradient endpoint assays, essentially as described [Wallace, A. and Corkill, J. (1989) Application of the spiral plating method to study antimicrobial action. *J. Microbiol. Meths.* 10, 303-310; Paton, J., Holt, A., and Bywater, M. (1990) Measurement of MICs of antibacterial agents by spiral gradient endpoint compared with conventional dilution methods. *Int. J. Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-100 µg/ml of test compound. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-compound concentration at the streak endpoint was calculated using the program SGE (Spiral Biotech, Inc.), and the MIC was defined as the calculated test-compound concentration at the streak endpoint.

Example 19

Assay of Antibacterial Efficacy in Mouse Model of *Staphylococcus aureus* Systemic Infection ("Peritonitis Model")

Female Swiss Webster mice were experimentally infected by intraperitoneal administration of $5 \times 10^7$ colony forming units of *Staphylococcus aureus* in 10% hog gastric mucin. Test compounds (2-3 mg/ml in vehicle [9-19% dimethyacetamide/8-16% Cremophor EL in water, v/v]), positive controls (2 mg/ml vancomycin in vehicle), and negative controls (vehicle only and saline only), were administered by intravenous injection into a tail vein 1 h and 5 h post-infection (200 µl per injection). Survival was monitored for 12 h post-infection, or for 24, 48, and 72 h post-infection. At the end of the monitoring period, surviving animals were euthanized.

Screening data for representative compounds of the invention are presented in the following Tables.

TABLE 3

| compound | IC50 E. coli RNAP (nM) | IC50 M. tuberculosis RNAP (nM) | IC50 S. aureus RNAP (nM) | MIC S. aureus 12600 (µg/ml) | MIC E. faecalis 19433 (µg/ml) | MIC A. baumannii 19606 (µg/ml) | MIC E. coli D21f2tolC (µg/ml) |
|---|---|---|---|---|---|---|---|
| Myx B | 13 | 130 | 66 | 0.78 | 13 | >40 | 0.098 |
| 7-desmethyl-Myx B | 22 | 81 | 140 | 3.1 | 25 | >40 | 0.195 |
| 1 | 12 | 85 | 52 | 1.4 | >40 | >40 | 0.3 |
| 2 | 11 | 70 | 23 | 1.4 | >40 | 25 | 0.23 |
| 3 | 6.8 | 270 | 17 | 2.4 | >40 | 5.6 | <0.18 |
| 4 | 4.6 | 320 | 8.3 | 9.4 | >40 | 3.1 | <0.18 |
| 5 | 3.9 | 32 | 15 | 0.44 | 12 | 19 | 0.076 |
| 6 | 3.9 | 47 | 12 | 0.45 | 13 | 5.5 | 0.076 |
| 7 | 63 | 450 | 93 | 12 | >40 | >40 | 0.37 |
| 8 | 4 | 19 | 9.2 | 0.5 | | | |
| 9 | 4.7 | 36 | 13 | 0.34 | 6.4 | 5.5 | 0.076 |
| 10 | 40 | 340 | 100 | 3.3 | >40 | >40 | 0.39 |

TABLE 4a

| compound | total dose (mg/kg) | 12-hour survival (%) |
|---|---|---|
| 5 in vehicle | 30 | 100 |
| 8 in vehicle | 30 | 75 |
| vancomycin in vehicle | 30 | 100 |
| vehicle | — | 0 |
| none | — | 0 | vehicle = 19% dimethylacetamide/8% Cremophor EL/73% water, v/v/v

TABLE 4b

| compound | total dose (mg/kg) | 12-hour survival (%) |
|---|---|---|
| Myx B in vehicle | 50 | 50 |
| vancomycin in vehicle | 30 | 100 |
| vehicle | — | 0 |
| none | — | 0 | vehicle = 19% dimethylacetamide/16% Cremophor EL/73% water, v/v/v

TABLE 4c

| compound | total dose (mg/kg) | 24-hour survival (%) | 48-hour survival (%) | 72-hour survival (%) |
|---|---|---|---|---|
| Myx B in vehicle | 50 | 75 | 50 | 50 |
| vancomycin in vehicle | 30 | 100 | 100 | 100 |
| vehicle | — | 0 | 0 | 0 |
| none | — | 0 | 0 | 0 | vehicle = 9% dimethylacetamide/8% Cremophor EL/83% water, v/v/v

The data in Table 3 indicate that at compounds 1-6 and 8-10 exhibit low nanomolar IC50s for inhibition of a bacterial RNA polymerase (IC50≤50 nM for *E. coli* RNA polymerase), and that compounds 4-6, 8, and 9 exhibit very low nanomolar IC50s for inhibition of a bacterial RNA polymerase (IC50≤5 nM for *E. coli* RNA polymerase).

The data in Table 3 also indicate that compounds 1-6, 8, and 9 inhibit a bacterial RNA polymerase more potently than Myx B and 7-desmethyl-Myx B.

The data in Table 3 also indicate that compounds 5, 6, 8, and 9 inhibit the Gram-positive bacterial pathogen *Staphylococcus aureus* more potently than Myx B and 7-desmethyl-Myx B.

The data in Table 3 also indicate that compounds 5 and 9 inhibit the Gram-positive bacterial pathogen *Enterococcus faecalis* more potently than Myx B and 7-desmethyl-Myx B.

The data in Table 3 also indicate that compounds 2-6 and 9 inhibit the Gram-negative bacterial pathogen *Acinetobacter baumannii*, which is not detectably inhibited by Myx B and 7-desmethyl-Myx B. This finding shows that at least some compounds of this invention not only exhibit an increased potency of inhibition of bacterial RNA polymerase and an increased potency of inhibition of bacterial growth, but also exhibit a broadened spectrum of antibacterial activity.

The data in Tables 4a-4-c indicate that compound 5, compound 8, and Myx B increase survival in a mouse model of *Staphylococcus aureus* infection.

The data in Tables 4a-4-c also indicate that compound 5, compound 8, and Myx B can be formulated for intravenous injection of a mammal at concentrations of at least 2 mg/ml in vehicles containing 9% to 19% dimethylacetamide and 8% to 16% Cremophor EL.

The data in Tables 4a-4-c also indicate that compound 5, compound 8, and Myx B can be administered by intravenous injection of a mammal at daily total doses of at least 30 mg/kg in vehicles containing 9% to 19% dimethylacetamide and 8% to 16% Cremophor EL.

The data in Tables 4a-4-c also indicate that compound 5, compound 8, and Myx B are tolerated without acute toxicity upon intravenous injection of a mammal at daily total doses of at least 30 mg/kg in vehicles containing 9% to 19% dimethylacetamide and 8% to 16% Cremophor EL.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of inhibiting a bacterial RNAP, comprising contacting a bacterial RNA polymerase with a compound of compound formula I:

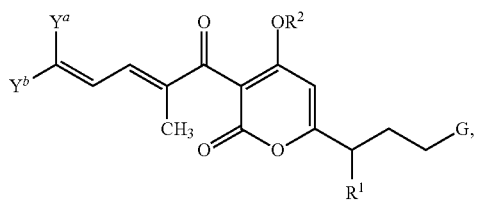

or a pharmaceutically acceptable salt thereof, wherein:
$R^1$ is hydrogen or —$CH_3$;
$R^2$ is hydrogen or —$C_1$-$C_6$ straight or branched alkyl;
one of $Y^a$ and $Y^b$ is hydrogen or $C_1$-$C_4$ straight alkyl, and the other of $Y^a$ and $Y^b$ is $C_1$-$C_{10}$ straight or branched alkyl, $C_2$-$C_{12}$ straight or branched hydroxyalkyl, $C_2$-$C_{12}$ straight or branched alkenyl, $C_2$-$C_{12}$ straight or branched hydroxyalkenyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $Y^a$ and $Y^b$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl or hydroxyalkyl groups, wherein an alkyl, aryl or heteroaryl moiety of $Y^a$ and $Y^b$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$ alkyl), and —$SO_2$($C_1$-$C_4$ alkyl);
G is —CH=CH—NHC(O)—$R^3$, —CH=CH—NHC(S)—$R^3$, —$CH_2CH_2$NHC(O)—$R^3$, —$CH_2CH_2$NHC(S)—$R^3$, —$CH_2$NHNHC(O)—$R^3$, or —$CH_2$NHNHC(S)—$R^3$;
$R^3$ is $C_1$-$C_6$ alkyl, —O($C_1$-$C_6$ alkyl), —S($C_1$-$C_6$ alkyl), or —N($R^4$)$_2$; and
each $R^4$ is independently hydrogen or —$C_1$-$C_6$ alkyl;
provided that, when $Y^a$ is hydrogen and $Y^b$ is —$CH_2CH_2CH_2CH_3$, or when $Y^a$ is —$CH_3$ and $Y^b$ is —$CH_2CH_2CH_3$, —$CH_2CH_2CH_2CH_3$, —$CH_2CH_2CH=C(CH_3)_2$, —$CH_2CH_2CH(OH)C(CH_3)=CHCH_2CH=CHCH_3$, or —$CH_2CH_2CH(OH)C(CH_3)=CHCH_2CH=CHCH_2CH_3$, then G is other than —CH=CH—NHC(O)—$OCH_3$; and
provided that, when $Y^a$ is —$CH_3$ and $Y^b$ is —$CH_2CH_2CH_2CH_3$, then G is other than —$CH_2CH_2$—NHC(O)—$OCH_3$.

2. A method of inhibiting a bacterial RNAP, comprising contacting a bacterial RNAP with a compound of formula I:

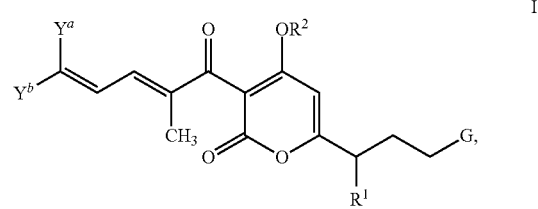

or a pharmaceutically acceptable salt thereof, wherein:
$R^1$ is hydrogen or —$CH_3$;
$R^2$ is hydrogen or —$C_1$-$C_6$ straight or branched alkyl;
one of $Y^a$ and $y^b$ is hydrogen or $C_1$-$C_4$ straight alkyl, and the other of $Y^a$ and $Y^b$ is $C_1$-$C_{10}$ straight or branched alkyl, $C_2$-$C_{12}$ straight or branched hydroxyalkyl, $C_2$-$C_{12}$ straight or branched alkenyl, $C_2$-$C_{12}$ straight or branched hydroxyalkenyl, phenyl, $C_7$-$C_{12}$ aralkyl, $C_7$-$C_{12}$ (aryl)hydroxyalkyl, $C_6$-$C_{12}$ heteroaralkyl, $C_6$-$C_{12}$ (heteroaryl)hydroxyalkyl, or $Y^a$ and $Y^b$ are taken together with their intervening atom to form a 4-6 membered ring having 0-1 ring heteroatoms selected from nitrogen, oxygen or sulfur, said ring optionally substituted by one or two $C_1$-$C_6$ alkyl, $C_2$-$C_6$ alkenyl or hydroxyalkyl groups, wherein an alkyl, aryl or heteroaryl moiety of $Y^a$ and $Y^b$ optionally is substituted with 1-3 groups independently selected from halo, —$C_1$-$C_6$ hydroxyalkyl, —$C_1$-$C_4$ alkoxy, —$C_1$-$C_4$ trifluoroalkoxy, —CN, —$C_1$-$C_4$ alkoxycarbonyl, —$C_1$-$C_4$ alkylcarbonyl, —S($C_1$-$C_4$alkyl), and —$SO_2$($C_1$-$C_4$ alkyl);
G is —CH=CH—NHC(O)—$R^3$, —CH=CH—NHC(S)—$R^3$, —$CH_2CH_2$NHC(O)—$R^3$, —$CH_2CH_2$NHC(S)—$R^3$, —$CH_2$NHNHC(O)—$R^3$, or —$CH_2$NHNHC(S)—$R^3$;
each $R^3$ is independently $C_1$-$C_6$ alkyl, —O($C_1$-$C_6$ alkyl), —S($C_1$-$C_6$ alkyl), or —N($R^4$)$_2$; and
each $R^4$ is independently hydrogen or —$C_1$-$C_6$ alkyl;
provided that, when $Y^a$ is hydrogen and $Y^b$ is —$CH_2CH_2CH_2CH_3$, or when $Y^a$ is —$CH_3$ and $Y^b$ is —$CH_2CH_2CH=C(CH_3)_2$, —$CH_2CH_2CH(OH)C$ (CH$_3$)=CHCH$_2$CH=CHCH$_3$, or —CH$_2$CH$_2$CH(OH)C(CH$_3$)=CHCH$_2$CH=CHCH$_2$CH$_3$, then G is other than —CH=CH—NHC(O)—OCH$_3$;

and provided that, when Y$^a$ is —CH$_3$ and Y$^b$ is —CH$_2$CH$_2$CH$_3$ or —CH$_2$CH$_2$CH$_2$CH$_3$, then G is other than —CH=CH—NHC(O)—(C$_1$-C$_6$ alkyl), —CH=CH—NHC(O)—O(C$_1$-C$_6$ alkyl), —CH=CH—NHC(O)—N(R$^4$)$_2$, and —CH$_2$CH$_2$—NHC(O)—O(C$_1$-C$_6$ alkyl).

3. The method of claim 1 wherein the bacterial RNAP is from *Mycobacterium tuberculosis, Mycobacterium avium, Staphylococcus aureus, Enterococcus faecalis, Enterococcus faecium, Streptococcus pneumoniae, Enterobacter cloacae, Clostridium difficile, Acinetobacter baumannii,* or *Escherichia coli*.

4. A method of treating a bacterial infection in a mammal, comprising administering to the mammal a therapeutically effective amount of a compound of formula I:

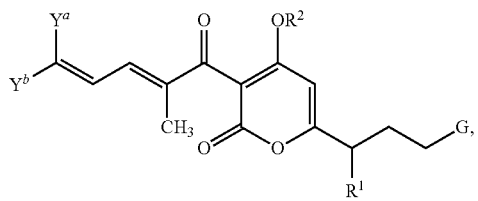

I or a pharmaceutically acceptable salt thereof, wherein:

R$^1$ is hydrogen or —CH$_3$;

R$^2$ is hydrogen or —C$_1$-C$_6$ straight or branched alkyl;

one of Y$^a$ and Y$^b$ is hydrogen or C$_1$-C$_4$ straight alkyl, and the other of Y$^a$ and Y$^b$ is C$_1$-C$_{10}$ straight or branched alkyl, C$_2$-C$_{12}$ straight or branched hydroxyalkyl, C$_2$-C$_{12}$ straight or branched alkenyl, C2-C$_{12}$ straight or branched hydroxyalkenyl, phenyl, C$_7$-C$_{12}$ aralkyl, C$_7$-C$_{12}$ (aryl)hydroxyalkyl, C$_6$-C$_{12}$ heteroaralkyl, C$_6$-C$_{12}$ (heteroaryl)hydroxyalkyl, or Y$^a$ and Y$^b$ are taken together with their intervening atom to form a 4-6 membered ring having 0-1 ring heteroatoms selected from nitrogen, oxygen or sulfur, said ring optionally substituted by one or two C$_1$-C$_6$ alkyl, C$_2$-C$_6$ alkenyl or hydroxyalkyl groups, wherein an alkyl, aryl or heteroaryl moiety of Y$^a$ and Y$^b$ optionally is substituted with 1-3 groups independently selected from halo, —C$_1$-C$_6$ hydroxyalkyl, —C$_1$-C$_4$ alkoxy, —C$_1$-C$_4$ trifluoroalkoxy, —CN, —C$_1$-C$_4$ alkoxycarbonyl, —C$_1$-C$_4$ alkylcarbonyl, —S(C$_1$-C$_4$ alkyl), and —SO$_2$(C$_1$-C$_4$ alkyl);

G is —CH=CH—NHC(O)—R$^3$, —CH=CH—NHC(S)—R$^3$, —CH$_2$CH$_2$NHC(O)—R$^3$, —CH$_2$CH$_2$NHC(S)—R$^3$, —CH$_2$NHNHC(O)—R$^3$, or —CH$_2$NHNHC(S)—R$^3$;

each R$^3$ is independently C$_1$-C$_6$ alkyl, —O(C$_1$-C$_6$ alkyl), —S(C$_1$-C$_6$ alkyl), or —N(R$^4$)$_2$; and each R$^4$ is independently hydrogen or —C$_1$-C$_6$ alkyl;

provided that, when Y$^a$ is hydrogen and Y$^b$ is —CH$_2$CH$_2$CH$_2$CH$_3$, or when Y$^a$ is —CH$_3$ and Y$^b$ is —CH$_2$CH$_2$CH=C(CH$_3$)$_2$, —CH$_2$CH$_2$CH(OH)C(CH$_3$)=CHCH$_2$CH=CHCH$_3$, or —CH$_2$CH$_2$CH(OH)C(CH$_3$)=CHCH$_2$CH=CHCH$_2$CH$_3$, then G is other than —CH=CH—NHC(O)—OCH$_3$;

and provided that, when Y$^a$ is —CH$_3$ and Y$^b$ is —CH$_2$CH$_2$CH$_3$ or —CH$_2$CH$_2$CH$_2$CH$_3$, then G is other than —CH=CH—NHC(O)—(C$_1$-C$_6$ alkyl), —CH=CH—NHC(O)—O(C$_1$-C$_6$ alkyl), —CH=CH—NHC(O)—N(R$^4$)$_2$, and —CH$_2$CH$_2$—NHC(O)—O(C$_1$-C$_6$ alkyl).

5. The method of claim 4 wherein the bacterial infection is associated with *Mycobacterium tuberculosis, Mycobacterium avium, Staphylococcus aureus, Enterococcus faecalis, Enterococcus faecium, Streptococcus pneumoniae, Enterobacter cloacae,* or *Clostridium difficile, Acinetobacter baumannii,* or *Escherichia coli*.

6. A composition comprising:

(a) from about 0.25 mg/ml to about 5 mg/ml of a compound of formula I:

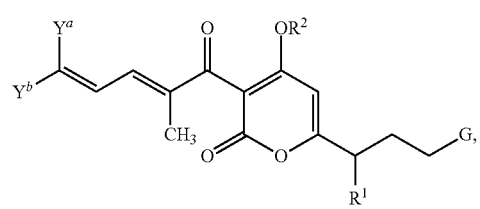

I or a pharmaceutically acceptable salt thereof, wherein:

R$^1$ is hydrogen or —CH$_3$;

R$^2$ is hydrogen or —C$_1$-C$_6$ straight or branched alkyl;

one of Y$^a$ and Y$^b$ is hydrogen or C$_1$-C$_4$ straight alkyl, and the other of Y$^a$ and Y$^b$ is C$_1$-C$_{10}$ straight or branched alkyl, C$_2$-C$_{12}$ straight or branched hydroxyalkyl, C$_2$-C$_{12}$ straight or branched alkenyl, C$_2$-C$_{12}$ straight or branched hydroxyalkenyl, phenyl, C$_7$-C$_{12}$ aralkyl, C$_7$-C$_{12}$ (aryl)hydroxyalkyl, C$_6$-C$_{12}$ heteroaralkyl, C$_6$-C$_{12}$ (heteroaryl)hydroxyalkyl, or Y$^a$ and Y$^b$ are taken together with their intervening atom to form a 4-6 membered ring having 0-1 ring heteroatoms selected from nitrogen, oxygen or sulfur, said ring optionally substituted by one or two C$_1$-C$_6$ alkyl, C$_2$-C$_6$ alkenyl or hydroxyalkyl groups, wherein an alkyl, aryl or heteroaryl moiety of Y$^a$ and Y$^b$ optionally is substituted with 1-3 groups independently selected from halo, —C$_1$-C$_6$ hydroxyalkyl, —C$_1$-C$_4$ alkoxy, —C$_1$-C$_4$ trifluoroalkoxy, —CN, —C$_1$-C$_4$ alkoxycarbonyl, —C$_1$-C$_4$ alkylcarbonyl, —S(C$_1$-C$_4$ alkyl), and —SO$_2$(C$_1$-C$_4$ alkyl);

G is —CH=CH—NHC(O)—R$^3$, —CH=CH—NHC(S)—R$^3$, —CH$_2$CH$_2$NHC(O)—R$^3$, —CH$_2$CH$_2$NHC(S)—R$^3$, —CH$_2$NHNHC(O)—R$^3$, or —CH$_2$NHNHC(S)—R$^3$;

R$^3$ is C$_1$-C$_6$ alkyl, —O(C$_1$-C$_6$ alkyl), —S(C$_1$-C$_6$ alkyl), or —N(R$^4$)$_2$; and each R$^4$ is independently hydrogen or —C$_1$-C$_6$ alkyl;

(b) about 5% to about 20% dimethylacetamide; and (c) about 4% to about 16% Cremophor EL.

7. The composition of claim 6 which comprises from about 0.5 mg/ml to about 3 mg/ml of the compound of formula I or a pharmaceutically acceptable salt thereof; about 5% to about 15% dimethylacetamide; and about 4% to about 12% Cremophor EL.

8. The composition of claim 6 which comprises about 2 mg/ml of the compound of formula I or a pharmaceutically acceptable salt thereof; about 9% dimethylacetamide; and about 8% Cremophor EL.

9. The composition of claim 6 wherein the compound of formula I is a compound of the following formula Ia:

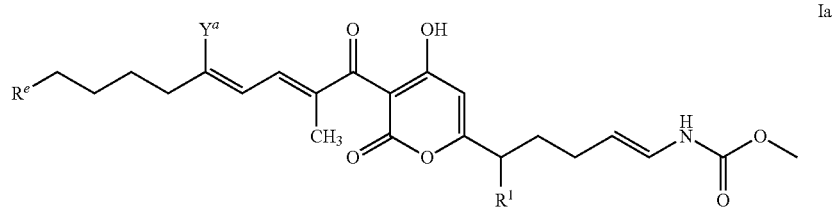
wherein: $R^e$ is H, methyl, or ethyl, which methyl or ethyl is optionally is substituted with hydroxy, —$C_1$-$C_4$ alkoxy, or halo; $Y^a$ is H or methyl; and $R^1$ is H or methyl.
* * * * *